(12) United States Patent
Abolmaesumi et al.

(10) Patent No.: US 11,129,591 B2
(45) Date of Patent: Sep. 28, 2021

(54) ECHOCARDIOGRAPHIC IMAGE ANALYSIS

(71) Applicant: THE UNIVERSITY OF BRITISH COLUMBIA, Vancouver (CA)

(72) Inventors: Purang Abolmaesumi, Vancouver (CA); Robert Rohling, Vancouver (CA); Amir H. Abdi, Vancouver (CA); Teresa S. M. Tsang, Vancouver (CA)

(73) Assignee: The University of British Columbia, Vancouver (CA)

( * ) Notice: Subject to any disclaimer, the term of this patent is extended or adjusted under 35 U.S.C. 154(b) by 500 days.

(21) Appl. No.: 16/095,601

(22) PCT Filed: Apr. 21, 2017

(86) PCT No.: PCT/CA2017/050496
§ 371 (c)(1),
(2) Date: Oct. 22, 2018

(87) PCT Pub. No.: WO2017/181288
PCT Pub. Date: Oct. 26, 2017

(65) Prior Publication Data
US 2019/0125298 A1    May 2, 2019

Related U.S. Application Data

(60) Provisional application No. 62/325,779, filed on Apr. 21, 2016.

(51) Int. Cl.
*G06K 9/00* (2006.01)
*A61B 8/08* (2006.01)
(Continued)

(52) U.S. Cl.
CPC .......... *A61B 8/0883* (2013.01); *A61B 8/4405* (2013.01); *A61B 8/463* (2013.01);
(Continued)

(58) Field of Classification Search
CPC ..... A61B 8/0883; A61B 8/463; A61B 8/4405; A61B 8/5215; G06N 3/04; G06N 3/08;
(Continued)

(56) References Cited

U.S. PATENT DOCUMENTS

| 5,776,063 A | 7/1998 | Dittrich et al. |
| 7,672,491 B2 | 3/2010 | Krishnan et al. |

(Continued)

FOREIGN PATENT DOCUMENTS

| WO | 2014097090 A1 | 6/2014 |
| WO | 2014/155272 A1 | 10/2014 |
| WO | 2017181288 A1 | 10/2017 |

OTHER PUBLICATIONS

Abdi, A.H. et al., "Automatic Quality Assessment of Apical Four-Chamber Echocardiograms Using Deep Convolutional Neural Networks", SPIE Medical Imaging 2017: Image Processing, edited by Martin A. Styner, Elsa D. Angelini, Proceedings of SPIE, vol. 10133, 101330S, Feb. 2017.

(Continued)

Primary Examiner — Nan D Huynh
(74) Attorney, Agent, or Firm — Kolitch Romano LLP

(57) ABSTRACT

A computer-implemented system for facilitating echocardiographic image analysis is disclosed. The system includes at least one processor configured to receive signals representing a first at least one echocardiographic image, associate the image with a first view category of a plurality of predetermined view categories, determine, based on the first at least one echocardiographic image and the first view category, a first quality assessment value representing a view category specific quality assessment of the first at least one echocardiographic image, and produce signals representing the first quality assessment value for causing the first quality assessment value to be associated with the first at least one echocardiographic image. The at least one processor may (Continued)

also be configured to do the above steps for a second at least one echocardiographic and a second view category that is different from the first view category image. Other systems, methods, and computer-readable media are also disclosed.

20 Claims, 20 Drawing Sheets

(51) Int. Cl.
  *A61B 8/00* (2006.01)
  *G06T 7/00* (2017.01)
  *G06N 3/04* (2006.01)
  *G06N 3/08* (2006.01)

(52) U.S. Cl.
  CPC .............. *G06N 3/04* (2013.01); *G06N 3/08* (2013.01); *G06T 7/0012* (2013.01); *G06N 3/082* (2013.01); *G06T 2207/10132* (2013.01); *G06T 2207/20081* (2013.01); *G06T 2207/20084* (2013.01); *G06T 2207/30048* (2013.01); *G06T 2207/30168* (2013.01)

(58) Field of Classification Search
  CPC .............. G06N 3/082; G06T 7/0012; G06T 2207/10132; G06T 2207/20081; G06T 2207/20084; G06T 2207/30048; G06T 2207/30168; G16H 50/20
  USPC ........................................................ 382/128
  See application file for complete search history.

(56) References Cited

U.S. PATENT DOCUMENTS

| | | | |
|---|---|---|---|
| 7,672,517 | B2 | 3/2010 | Buscema |
| 7,680,308 | B2 | 3/2010 | Dale |
| 7,912,528 | B2 | 3/2011 | Krishnan et al. |
| 8,594,398 | B2 | 11/2013 | Beymer et al. |
| 8,712,157 | B2 | 4/2014 | Marchesotti et al. |
| 8,744,152 | B2 | 6/2014 | Beymer et al. |
| 8,750,375 | B2 | 6/2014 | Beymer et al. |
| 8,891,881 | B2 | 11/2014 | Gupta et al. |
| 8,917,917 | B2 | 12/2014 | Beymer et al. |
| 9,652,846 | B1 | 5/2017 | Codella et al. |
| 9,918,701 | B2 | 3/2018 | Hedlund et al. |
| 10,074,038 | B2 | 9/2018 | Hsieh et al. |
| 10,127,659 | B2 | 11/2018 | Hsieh et al. |
| 10,140,734 | B2 | 11/2018 | Chen |
| 10,242,443 | B2 | 3/2019 | Hsieh et al. |
| 2005/0020903 | A1* | 1/2005 | Krishnan .............. G16H 50/20 600/407 |
| 2005/0251013 | A1* | 11/2005 | Krishnan .............. G06T 7/0012 600/407 |
| 2006/0147107 | A1 | 7/2006 | Zhang et al. |
| 2009/0034808 | A1 | 2/2009 | Zhou et al. |
| 2009/0074280 | A1* | 3/2009 | Lu .......................... A61B 8/523 382/131 |
| 2009/0088640 | A1* | 4/2009 | Park ..................... G06K 9/6257 600/453 |
| 2010/0168578 | A1 | 7/2010 | Garson, Jr. et al. |
| 2011/0082371 | A1 | 4/2011 | Chono |
| 2015/0005629 | A1* | 1/2015 | Monahan .............. A61B 8/481 600/431 |
| 2015/0025666 | A1* | 1/2015 | Olivieri .................. G06F 30/00 700/98 |
| 2015/0086093 | A1 | 3/2015 | Fonte et al. |
| 2015/0302638 | A1 | 10/2015 | Jago et al. |
| 2017/0026298 | A1 | 1/2017 | Huo |
| 2017/0143312 | A1 | 5/2017 | Hedlund et al. |
| 2017/0360401 | A1 | 12/2017 | Rothberg et al. |
| 2017/0360402 | A1 | 12/2017 | DeJonge et al. |
| 2017/0360403 | A1 | 12/2017 | Rothberg et al. |
| 2017/0360411 | A1 | 12/2017 | Rothberg et al. |
| 2017/0360412 | A1 | 12/2017 | Rothberg et al. |
| 2018/0144214 | A1 | 5/2018 | Hsieh et al. |
| 2018/0153505 | A1 | 6/2018 | Cadieu et al. |

OTHER PUBLICATIONS

Hochreiter, Set al., "Long Short-Term Memory"; Neural Computation 1735-1780, 1997.
Ioffe, Sergey et al., "Batch Normalization: Accelerating Deep Network Training by Reducing Internal Covariate Shift" Proceedings of the 32nd International Conference on Machine Learning; ICML'15, JMLR Mar. 2, 2015.
Lu, Xiaoguang et al., "AutoMPR: Automatic Detection of Standard Planes in 3D Echocardiography"; 5th IEEE International Symposium on ISBI 2008.
Nair, Vinod et al., "Rectified Linear Units Improve Restricted Boltzmann Machines"; Proceedings of the 27th International Conference on Machine Learning (ICML-10) 2010.
Pavani, Sri-Kaushik et al., "Quality Metric for Parasternal Long Axis B-Mode Echocardiograms," Published in Medical Image Computing and Computer Assisted Intervention (MICCAI); vol. 15, Part 2; 2012.
Search Strategy in PCT Application No. PCT/CA2019/051192 mailed Nov. 8, 2019.
International Search Report dated Nov. 2019 for Application No. PCT/CA2019/051192, 3 pages.
Written Opinion of the International Searching Authority dated Nov. 8, 2019 for Application No. PCT/CA2019/051192, 5 pages.
Nov. 8, 2019, Extended European Search Report from the European Patent Office in European Patent Application Serial No. 17785210.0, which is a foreign counterpart to this application.
A. S. Miller, et al., "Review of Neural Network Applications in Medical Imaging and Signal Processing," published in Medical & Biological Engineering & Computing in Sep. 1992. vol. 30, pp. 449-464.
R. H. Clayton, et al., "Recognition of Ventricular Fibrillation Using Neural Networks," published in Medical & Biological Engineering & Computing in Mar. 1994. vol. 32, pp. 217-220.
Diptiitchhaporia, MD; et al., "Artificial Neural Networks: Current Status in Cardiovascular Medicine," published in the Journal of the American College of Cardiology (JACC) in Aug. 1996. vol. 28, issue 2, pp. 515-521.
Curt G. Degroff, MD; et al., "Artificial Neural Network-Based Method of Screening Heart Murmurs in Children," published in Circulation by the American Heart Association on Jun. 5, 2001. vol. 103, issue 22, pp. 2711-2716.
S. Kevin Zhou, et al., "Image-based Multiclass Boosting and Echocardiographic View Classification," in 2006 IEEE Computer Society Conference on Computer Vision and Pattern Recognition (CVPR'06). vol. 2, pp. 1559-1565.
Alison Noble, et al., "Ultrasound Image Segmentation: A Survey," published in IEEE Transactions on Medical Imaging from the Institute of Electrical and Electronics Engineers in Aug. 2006. vol. 25, issue 8, pp. 987-1010.
Xiaoguang Lu, et al., "AutoMPR: Automatic Detection of Standard Planes in 3D Echocardiography," published in 2008 5th IEEE International Symposium on Biomedical Imaging: From Nano to Macro in Jun. 2008. pp. 1279-1282.
J. Jiang, et al., "Medical Imaging Analysis with Artificial Neural Networks," published in Computerized Medical Imaging and Graphics in 2010. vol. 34, issue 8, pp. 617-631.
Neelam Sinha, et al., "Quality Assessment in Magnetic Resonance Images," published in Critical Reviews™ in Biomedical Engineering (CRMBE) in 2010. vol. 38, issue 2, pp. 127-141.
Sri-Kaushik Pavani, et al., "Quality Metric for Parasternal Long Axis B-Mode Echocardiograms," published in Medical Image Computing and Computer Assisted Intervention (MICCAI) in Jan. 2012. vol. 15, part 2, pp. 478-485.
Xiaoming Liu, et al., "Learning-based Scan Plane Identification from Fetal Head Ultrasound Images," published in Medical Imaging 2012: Ultrasonic Imaging, Tomography, and Therapy; 83200A in Feb. 2012. Proceedings SPIE vol. 8320.

(56) References Cited

OTHER PUBLICATIONS

Sten Roar Snare, et al., "Real-Time Scan Assistant for Echocardiography," in IEEE Transactions on Ultrasonics, Ferroelectrics, and Frequency Control in Mar. 2012. vol. 59, issue 3, pp. 583-589.

Shijun Wang, et al., "Machine Learning and Radiology," published in Medical Image Analysis by Elsevier in Jul. 2012. vol. 16, issue 5, pp. 993-951.

Noha El-Zehiry, et al., "Learning the Manifold of Quality Ultrasound Acquisition," published in Medical Image Computing and Computer Assisted Intervention, Part 1 (MCCAI) in Sep. 2013.

Nima Torbati, et al., "An Efficient Neural Network Based Method for Medical Image Segmentation," published in Computers in Biology and Medicine by Elsevier on Jan. 1, 2014. vol. 44, pp. 76-87.

Hoo-Chang Shin, et al., "Deep Convolutional Neural Networks for Computer-Aided Detection: CNN Architectures, Dataset Characteristics and Transfer Learning," submitted to https://www.arXiv.org on Feb. 10, 2016.

Hao Chen, et al., "Iterative Multi-domain Regularized Deep Learning for Anatomical Structure Detection and Segmentation from Ultrasound Images," submitted to Medical Image Computing and Computer Assisted Intervention, Part 2 (MICCAI) in Jul. 2016.

Timothy J. W. Dawes, FRCA, PhD; et al., "Machine Learning of Three-dimensional Right Ventricular Motion Enables Outcome Prediction in Pulmonary Hypertension: A Cardiac MR Imaging Study," published online in Radiology in Jan. 2017.

Canadian Intellectual Property Office, International Search Report and Written Opinion of the International Searching Authority in PCT/CA2017/050496, dated Jul. 13, 2017, which is the international application to this U.S. application.

\* cited by examiner

240

Image file

242 — Image ID             2017042112000000
243 — Image group ID       1
244 — Image data

300

View category record

302 — View category ID      AP4
304 — Image group ID        1

Common neural network record

324 {
- Layer number: 1
- Layer type: Convolutional
- Stride: 1
- Kernel 1: [...]
- ...
- Kernel 8: [...]

326 {
- Layer number: 2
- Layer type: Max pool
- Stride: 2
- Kernel size: 2x2

328 {
- Layer number: 3
- Layer type: Convolutional
- Stride: 1
- Kernel 1: [...]
- ...
- Kernel 16: [...]

330 {
- Layer number: 4
- Layer type: Max pool
- Stride: 2
- Kernel size: 2x2

332 {
- Layer number: 5
- Layer type: Convolutional
- Stride: 1
- Kernel 1: [...]
- ...
- Kernel 32: [...]

334 {
- Layer number: 6
- Layer type: Max pool
- Stride: 2
- Kernel size: 2x2

View category specific neural network record

| | | |
|---|---|---|
| 342 — | View category ID | AP4 |
| 344 { | Layer number | 7 |
| | Layer type | Convolutional |
| | Stride | 1 |
| | Kernel 1 | [...] |
| | ... | |
| | Kernel 32 | [...] |
| 346 { | Layer number | 8 |
| | Layer type | Convolutional |
| | Stride | 1 |
| | Kernel 1 | [...] |
| | ... | |
| | Kernel 32 | [...] |
| 348 { | Layer number | 9 |
| | Layer type | Max pool |
| | Stride | 2 |
| | Kernel size | 2x2 |
| 350 { | Layer number | 10 |
| | Layer type | LSTM |
| | LSTM parameters | [...] |

420

Quality assessment record

422 — Image group ID      1
424 — Quality assessment      3.08

Training image file

742 — Image ID      2015082018120000
744 — Image group ID      1
746 — View category ID      AP4
748 — Image data

780

Expert quality assessment record

782 — Image group ID      1
784 — Expert quality assessment      4

ECHOCARDIOGRAPHIC IMAGE ANALYSIS

RELATED APPLICATION

This application claims the benefit of U.S. Provisional Application No. 62/325,779 entitled "PROCESS FOR IMAGING QUALITY ASSURANCE", filed on Apr. 21, 2016, which is hereby incorporated by reference herein in its entirety.

BACKGROUND

1. Field

Embodiments of this invention relate to echocardiographic image analysis and more particularly to echocardiographic image analysis for image quality assessment.

2. Description of Related Art

Despite advances in medicine and technology, cardiovascular disease remains the leading cause of mortality worldwide. Cardiac ultrasound, better known as echocardiography (echo), is the standard method for screening, detection, and monitoring of cardiovascular disease. This noninvasive imaging modality is widely available, cost-effective, and may be used for clinical measurement of anatomical features which may then be used for evaluation of cardiac structure and/or function. Some existing echocardiographic systems may be configured to provide feedback regarding general properties of captured images. However, this feedback may not assist echocardiographers in capturing high quality echocardiographic images for use in subsequent quantified clinical measurement of anatomical features.

SUMMARY

In accordance with one embodiment, there is provided a computer-implemented system for facilitating echocardiographic image analysis. The system includes at least one processor configured to, receive signals representing a first at least one echocardiographic image, associate the first at least one echocardiographic image with a first view category of a plurality of predetermined echocardiographic image view categories, determine, based on the first at least one echocardiographic image and the first view category, a first quality assessment value representing a view category specific quality assessment of the first at least one echocardiographic image, produce signals representing the first quality assessment value for causing the first quality assessment value to be associated with the first at least one echocardiographic image, receive signals representing a second at least one echocardiographic image, associate the second at least one echocardiographic image with a second view category of the plurality of predetermined echocardiographic image view categories, said second view category being different from the first view category, determine, based on the second at least one echocardiographic image and the second view category, a second quality assessment value representing a view category specific quality assessment of the second at least one echocardiographic image, and produce signals representing the second quality assessment value for causing the second quality assessment value to be associated with the second at least one echocardiographic image.

In accordance with another embodiment, there is provided a computer-implemented system for training neural networks to facilitate echocardiographic image analysis. The system includes at least one processor configured to: receive signals representing a plurality of echocardiographic training images, each of the plurality of echocardiographic training images associated with one of a plurality of predetermined echocardiographic image view categories, receive signals representing expert quality assessment values representing view category specific quality assessments of the plurality of echocardiographic training images, each of the expert quality assessment values provided by an expert echocardiographer and associated with one of the plurality of echocardiographic training images, and train the neural networks using the plurality of echocardiographic training images and the associated expert quality assessment values to determine sets of neural network parameters defining the neural networks, at least a portion of each of said neural networks associated with one of the plurality of predetermined echocardiographic image view categories.

In accordance with another embodiment, there is provided a computer-implemented method of facilitating echocardiographic image analysis. The method includes receiving signals representing a first at least one echocardiographic image, associating the first at least one echocardiographic image with a first view category of a plurality of predetermined echocardiographic image view categories, determining, based on the first at least one echocardiographic image and the first view category, a first quality assessment value representing a view category specific quality assessment of the first at least one echocardiographic image, producing signals representing the first quality assessment value for causing the first quality assessment value to be associated with the first at least one echocardiographic image, receiving signals representing a second at least one echocardiographic image, associating the second at least one echocardiographic image with a second view category of the plurality of predetermined echocardiographic image view categories, said second view category being different from the first view category, determining, based on the second at least one echocardiographic image and the second view category, a second quality assessment value representing a view category specific quality assessment of the second at least one echocardiographic image, and producing signals representing the second quality assessment value for causing the second quality assessment value to be associated with the second at least one echocardiographic image.

In accordance with another embodiment, there is provided a computer-implemented method of training neural networks to facilitate echocardiographic image analysis. The method includes receiving signals representing a plurality of echocardiographic training images, each of the plurality of echocardiographic training images associated with one of a plurality of predetermined echocardiographic image view categories, receiving signals representing expert quality assessment values representing view category specific quality assessments of the plurality of echocardiographic training images, each of the expert quality assessment values provided by an expert echocardiographer and associated with one of the plurality of echocardiographic training images, and training the neural networks using the plurality of echocardiographic training images and the associated expert quality assessment values to determine sets of neural network parameters defining the neural networks, at least a portion of each of said neural networks associated with one of the plurality of predetermined echocardiographic image view categories.

In accordance with another embodiment, there is provided a computer readable medium having stored thereon codes which when executed by at least one processor cause the at least one processor to perform any of the above methods.

In accordance with another embodiment, there is provided a system for facilitating echocardiographic image analysis. The system includes means for receiving signals representing a first at least one echocardiographic image, means for associating the first at least one echocardiographic image with a first view category of a plurality of predetermined echocardiographic image view categories, means for determining, based on the first at least one echocardiographic image and the first view category, a first quality assessment value representing a view category specific quality assessment of the first at least one echocardiographic image, means for producing signals representing the first quality assessment value for causing the first quality assessment value to be associated with the first at least one echocardiographic image, means for receiving signals representing a second at least one echocardiographic image, means for associating the second at least one echocardiographic image with a second view category of the plurality of predetermined echocardiographic image view categories, said second view category being different from the first view category, means for determining, based on the second at least one echocardiographic image and the second view category, a second quality assessment value representing a view category specific quality assessment of the second at least one echocardiographic image, and means for producing signals representing the second quality assessment value for causing the second quality assessment value to be associated with the second at least one echocardiographic image.

In accordance with another embodiment, there is provided a system for training neural networks to facilitate echocardiographic image analysis. The system includes means for receiving signals representing a plurality of echocardiographic training images, each of the plurality of echocardiographic training images associated with one of a plurality of predetermined echocardiographic image view categories, means for receiving signals representing expert quality assessment values representing view category specific quality assessments of the plurality of echocardiographic training images, each of the expert quality assessment values provided by an expert echocardiographer and associated with one of the plurality of echocardiographic training images, and means for training the neural networks using the plurality of echocardiographic training images and the associated expert quality assessment values to determine sets of neural network parameters defining the neural networks, at least a portion of each of said neural networks associated with one of the plurality of predetermined echocardiographic image view categories. Other aspects and features of embodiments of the invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention,

FIG. 7 is a representation of an exemplary view category record that may be used in the system shown in FIG. 1;

FIG. 9 is a representation of an exemplary common neural network record that may be used in the system shown in FIG. 1;

FIG. 12 is a representation of an exemplary quality assessment record that may be used in the system shown in FIG. 1;

DETAILED DESCRIPTION

Figure 1:
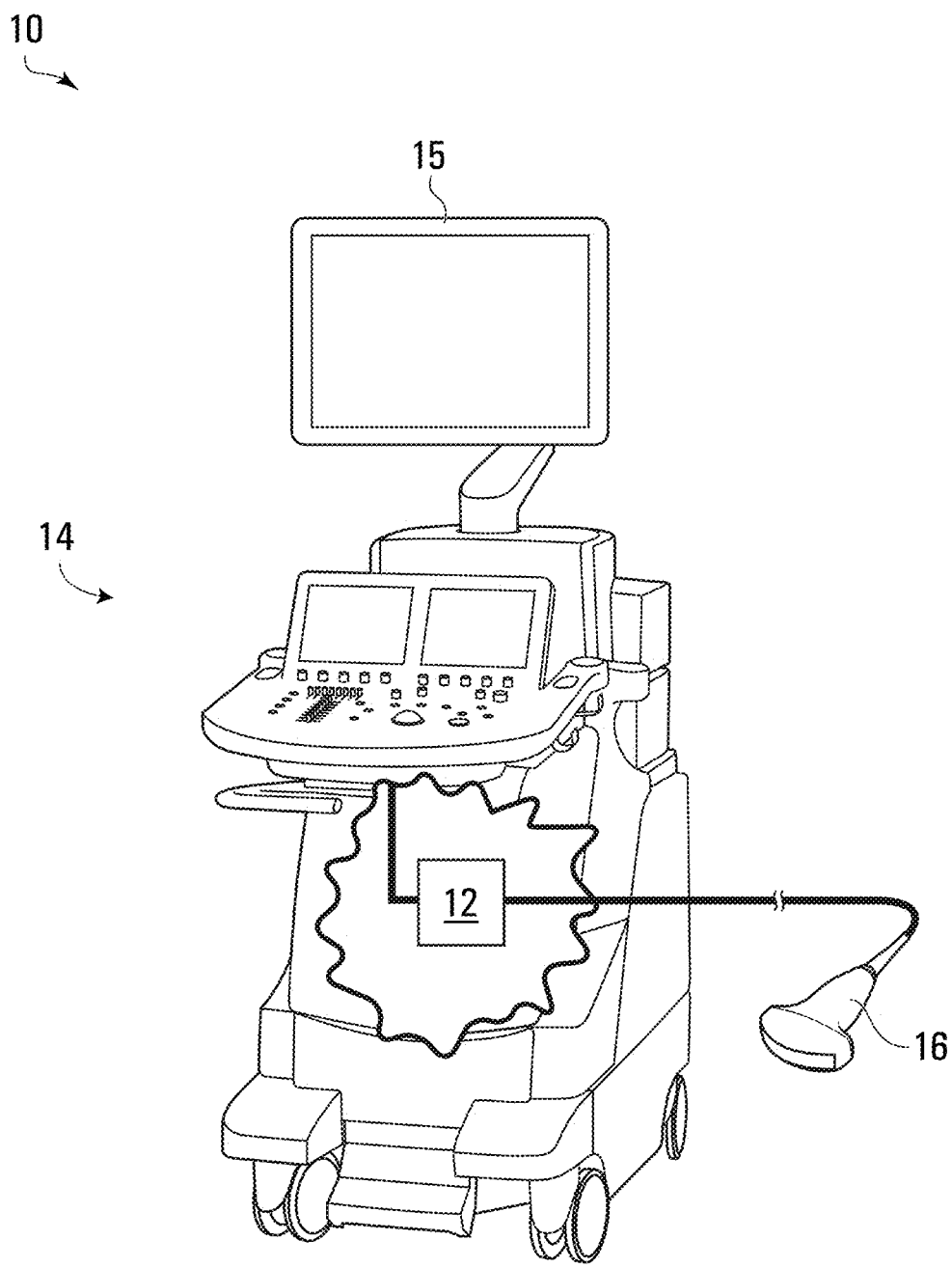
FIG. 1 is a schematic view of a system for facilitating echocardiographic image analysis in accordance with various embodiments of the invention.

Referring to FIG. 1, according to one embodiment of the invention, there is provided a system 10 for facilitating echocardiographic image analysis. The system 10 includes a computer-implemented echocardiographic image analyzer 12 in communication with a user interface system 14 and a transducer 16. In the embodiment shown, the analyzer 12 is also in communication with a network 126 and the user interface system 14 includes a display 15. In various embodiments, the system 10 may be incorporated within an ultrasound machine or scanner. For example, in various embodiments, the system 10 may be included in an ultrasound machine generally similar to a Philips™ IE33 Ultrasound machine or a mobile ultrasound machine made by Clarius™.

In operation, an operator of the system 10, who may be for example, an echocardiographer, technician, or sonographer, may manipulate the transducer 16 on or around a patient, and the analyzer 12 may communicate with the transducer 16 and receive signals representing echocardiographic images of the patient. The analyzer 12 may store representations of the echocardiographic images in memory and/or output representations of the images on the display 15. The analyzer 12 may determine a quality assessment value representing a quality assessment of at least one echocardiographic image and produce signals for causing the quality assessment value to be associated with the at least one echocardiographic image. For example, the analyzer 12 may be configured to produce signals for causing the display 15 to display a sequence of echocardiographic images captured by the analyzer 12 in near real-time, in association with the determined quality assessment value for the images. In some embodiments, the quality assessment value may be determined for a single image. In some embodiments, the quality assessment value may be determined for a sequence of images or video, which may be referred to herein as an echo cine.

In various embodiments, this near real-time feedback to the operator may help the operator improve their skills and/or improve image quality for subsequently captured images. For example, in some embodiments, the operator may, in response to viewing a low quality assessment value on the display 15, adjust positioning of the transducer and/or adjust image capture parameters, such as, for example, depth, focus, gain, frequency, and/or another parameter which may affect image quality in the system 10. The operator may make such adjustments until a high quality assessment value is provided on the display 15, for example, at which point the operator may be confident that the echocardiographic images captured are suitable for subsequent quantified clinical measurement of anatomical features and/or to assist in diagnosing a medical condition or a characteristic of the heart.

In various embodiments, the operator may wish to capture echocardiographic images for various views or anatomical planes since multiple views may be required in order to perform certain quantified clinical measurement of anatomical features and/or to assist in diagnosing a medical condition or a characteristic of the heart. In some embodiments, the views required for certain measurements or diagnoses may be chosen from standard 2D echocardiographic views. For example, the operator may wish to capture echocardiographic images of multiple standard 2D echocardiographic views to facilitate image analysis to determine ejection fraction for the patient's heart. For example, in some embodiments, a 2D Method of Simpson may be used to determine ejection fraction, which requires images from AP2 (apical 2-chamber view) and AP4 (apical 4-chamber view).

In various embodiments, some of the desirable characteristics for each of the different views may differ and so it may be desirable to determine quality assessment values for the echocardiographic images in different ways, depending on what view the echocardiographic images are meant to represent. Accordingly, the analyzer 12 may be configured to associate each set of echocardiographic images with a view category of a plurality of predetermined echocardiographic image view categories and to select and apply a function to the set of images to determine the quality assessment value wherein the function selected depends on the view category associated with the set of images. In some embodiments, the analyzer 12 may be configured to automatically determine the view category to associate with the set of images by analyzing the set of images. In some embodiments, the analyzer 12 may be configured to receive operator input (via the user interface system 14, for example), which sets the view category with which to associate the image.

Applying the function to a set of images may involve inputting the set of images into a view category specific image assessment neural network which is configured to output a view category specific quality assessment value. The quality assessment value may represent an assessment of suitability of the associated set of echocardiographic images for quantified clinical measurement of anatomical features.

Image Analyzer—Processor Circuit

Figure 2:
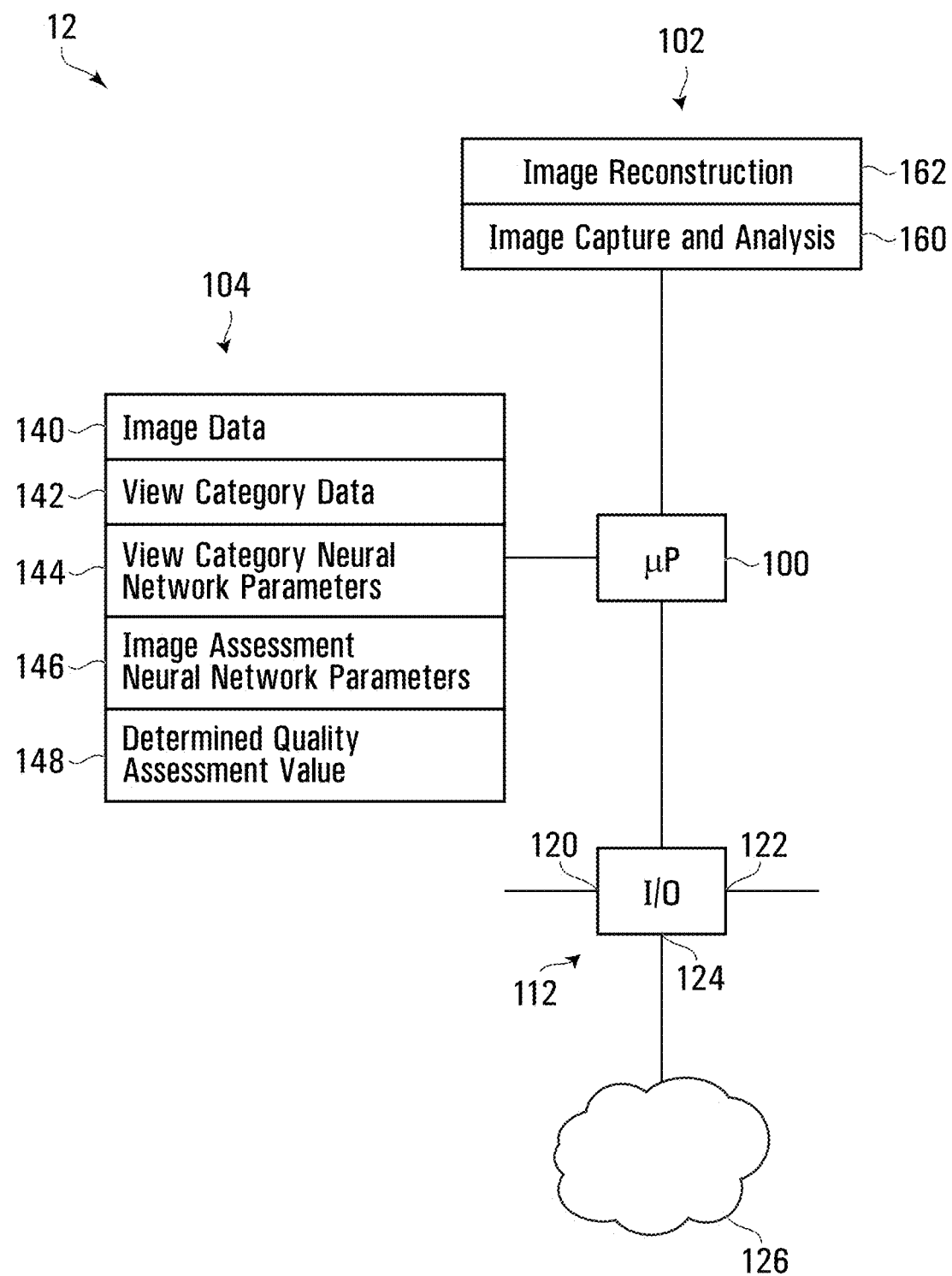
FIG. 2 is a schematic view of an echocardiographic image analyzer of the system of FIG. 1 including a processor circuit in accordance with various embodiments of the invention.

Referring now to FIG. 2, a schematic view of the analyzer 12 of the system 10 shown in FIG. 1 according to an embodiment is shown. As discussed above, in various embodiments, the analyzer 12 may be included in an ultrasound machine, for example.

Referring to FIG. 2, the analyzer 12 includes a processor circuit including an analyzer processor 100 and a program memory 102, a storage memory 104, and an input/output (I/O) interface 112, all of which are in communication with the analyzer processor 100. In various embodiments, the analyzer processor 100 may include one or more processing units, such as for example, a central processing unit (CPU), a graphical processing unit (GPU), and/or a field programmable gate arrays (FPGA). In some embodiments, any or all of the functionality of the analyzer 12 described herein may be implemented using one or more FPGAs.

The I/O interface 112 includes an interface 120 for communicating with the transducer 16 and an interface 122 for communicating with the user interface system 14 shown in FIG. 1. In some embodiments, the I/O interface 112 may also include an interface 124 for facilitating networked communication through the network 126. In some embodiments, any or all of the interfaces 120, 122, or 124 may facilitate a wireless or wired communication.

In some embodiments, the I/O interface 112 may include a network interface device or card with an input/output for connecting to the network 126, through which communications may be conducted with devices connected to the network 126, such as the neural network trainer (as shown at 502 in FIG. 14), for example.

In some embodiments, each of the interfaces shown in FIG. 2 may include one or more interfaces and/or some or all of the interfaces included in the I/O interface 112 may be implemented as combined interfaces or a single interface.

In some embodiments, where a device is described herein as receiving or sending information, it may be understood that the device receives signals representing the information via an interface of the device or produces signals representing the information and transmits the signals to the other device via an interface of the device.

Processor-executable program codes for directing the analyzer processor 100 to carry out various functions are stored in the program memory 102. Referring to FIG. 2, the program memory 102 includes a block of codes 160 for directing the analyzer 12 to perform image capture functions and analysis functions and a block of codes 162 for directing the analyzer processor 100 to perform image reconstruction functions. In this specification, it may be stated that certain encoded entities such as applications or modules perform certain functions. Herein, when an application, module or encoded entity is described as taking an action, as part of, for example, a function or a method, it will be understood that at least one processor (e.g. the analyzer processor 100) is directed to take the action by way of programmable codes or processor-executable codes or instructions defining or forming part of the application.

The storage memory 104 includes a plurality of storage locations including location 140 for storing image data, location 142 for storing view category data, location 144 for storing view category neural network parameter data, location 146 for storing image assessment neural network parameter data, and location 148 for storing determined quality assessment value data. In various embodiments, the plurality of storage locations may be stored in a database in the storage memory 104.

In various embodiments, the blocks of codes 160 and 162 may be integrated into a single block of codes and/or each of the blocks of code 160 and 162 may include one or more blocks of code stored in one or more separate locations in program memory 102. In various embodiments, any or all of the locations 140, 142, 144, and 146 may be integrated and/or each may include one or more separate locations in the storage memory 104.

Each of the program memory 102 and storage memory 104 may be implemented as one or more storage devices including random access memory (RAM), a hard disk drive (HDD), a solid-state drive (SSD), a network drive, flash memory, a memory stick or card, any other form of non-transitory computer-readable memory or storage medium, and/or a combination thereof. In some embodiments, the program memory 102, the storage memory 104, and/or any portion thereof may be included in a device separate from the analyzer 12 and in communication with the analyzer 12 via the I/O interface 112, for example.

In various embodiments, other device components described herein, such as memory, program memory, blocks of code, storage memory, locations in memory, and/or I/O interfaces, may be implemented generally similarly to as described above for the analyzer 12.

Image Analysis

Figure 3:
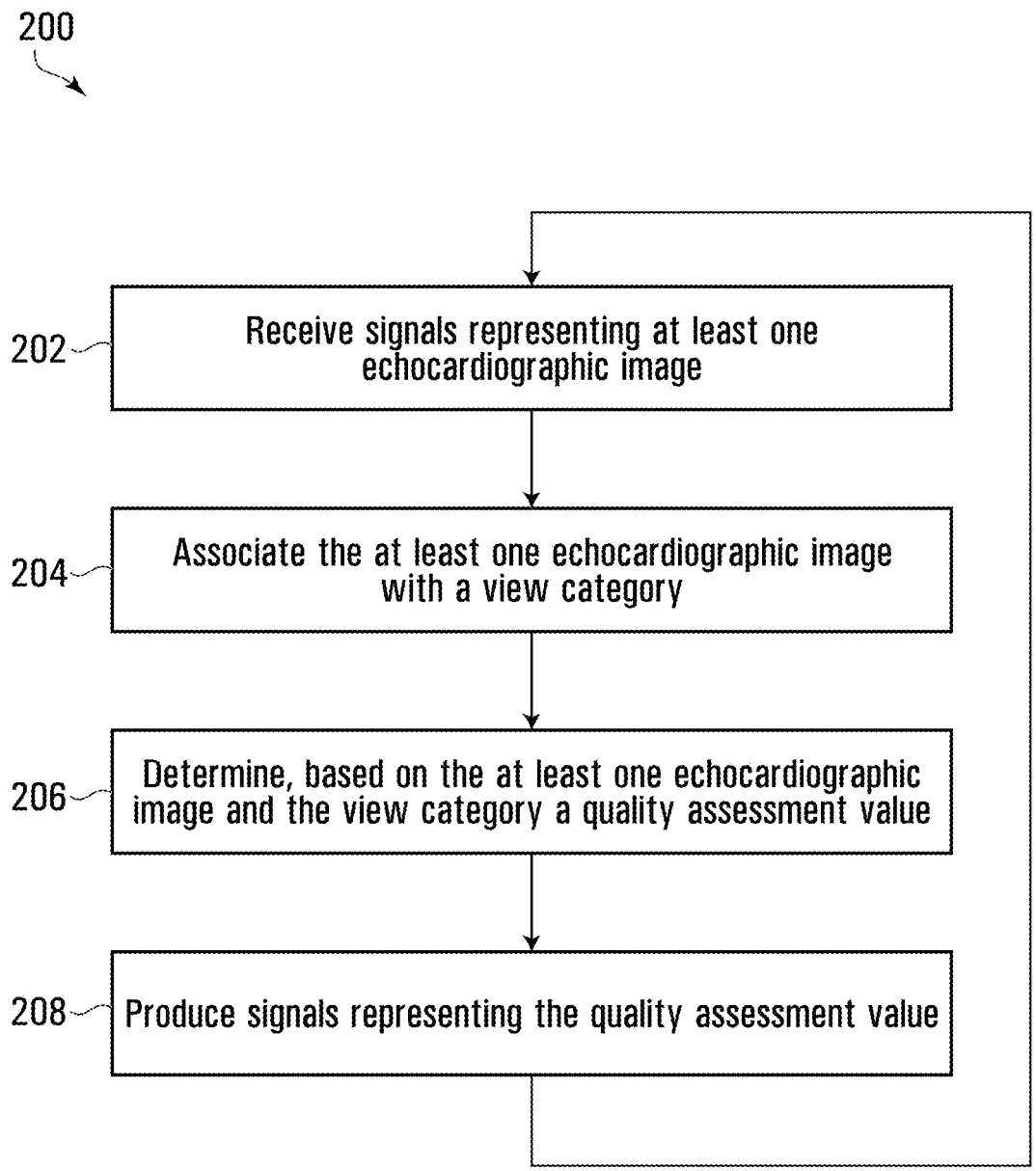
FIG. 3 is a flowchart depicting blocks of code for directing the analyzer of the system of FIG. 1 to perform image analysis functions in accordance with various embodiments of the invention.

Referring now to FIG. 3, a flowchart depicting blocks of code for directing the analyzer processor 100 shown in FIG. 2 to perform image analysis functions in accordance with one embodiment is shown generally at 200. The blocks of code included in the flowchart 200 may be encoded in the block of codes 160 of the program memory 102 shown in FIG. 2 for example.

Referring to FIG. 3, the flowchart 200 begins with block 202 which directs the analyzer processor 100 shown in FIG. 2 to receive signals representing at least one echocardiographic image. In various embodiments, block 202 may direct the analyzer processor 100 to obtain image data via the transducer 16. For example, block 202 may direct the analyzer processor 100 to execute blocks included in the block of codes 162 of the program memory 102, to cause the analyzer processor 100 to receive signals representing at least one echocardiographic image from the transducer 16 shown in FIG. 1 via the interface 120 of the I/O interface. The blocks in the block of codes 162 of the program memory 102 may direct the analyzer processor 100 to interpret raw ultrasound echo waveforms received from the transducer 16 into fully formed images. The block of codes 162 may direct the analyzer processor 100 to use an image reconstruction algorithm to filter the waveforms, amplify the waveforms, time delay and sum the waveforms, demodulate the summed waveforms, and/or compress amplitudes of the summed waveforms. The block of codes 162 may direct the analyzer processor 100 to finally perform a scan-conversion of the waveforms to derive an image in Cartesian coordinates with pixels of known size in millimeters.

Block 202 may direct the analyzer processor 100 to store a representation of the received at least one echocardiographic image in the location 140 of the storage memory 104.

In some embodiments, the analyzer 12 may be configured to receive and analyze respective sequences of echocardiographic images (echo cines). Accordingly, block 202 may direct the analyzer processor 100 to receive a sequence of images. Block 202 may direct the analyzer processor 100 to store a set of image files representing the sequence of images in the location 140 of the storage memory 104. An exemplary image file which may be included in the set of image files received at block 202 is shown at 240 in FIG. 4.

Figure 4:
FIG. 4 is a representation of an exemplary image file that may be used in the system shown in FIG. 1.

Referring to FIG. 4, the image file 240 includes an image identifier field 242 for storing a unique identifier for identifying the image data stored in the image file 240, an image group identifier field 243 for storing an identifier common to a set of image files which are to be analyzed together (e.g. frames of an echo cine), and an image data field 244 for storing information representing an image. In some embodiments, for example, the image file 240 may store a PNG file type representation of the echocardiographic image.

In some embodiments, block 202 may direct the analyzer processor 100 to receive and store a plurality of image files generally similar to the image file 240 shown in FIG. 4 in the location 140 of storage memory 104 for analysis together during execution of block 206 of the flowchart 200 shown in FIG. 3. For example, in some embodiments, the analyzer 12 may be configured to analyze a sequence of 20 images during execution of block 206 of the flowchart 200 and so block 202 may direct the analyzer processor 100 to store the received images as groups of 20 image files, each generally similar in format to the image file 240 shown in FIG. 4 and sharing a common value in their image group identifier fields.

Referring back to FIG. 4, block 204 then directs the analyzer processor 100 to associate the at least one echocardiographic image received at block 202 with a view category of a plurality of predetermined echocardiographic image view categories. In some embodiments, block 204 may direct the analyzer processor 100 to associate the at least one echocardiographic image with the view category by storing in the location 142 of the storage memory 104 a view category record that associates the view category with the received at least one echocardiographic image.

In various embodiments, associating the at least one echocardiographic image with a particular view category may assist with subsequent quality assessment of the echocardiographic images which may be performed at block 206 of the flowchart 200 shown in FIG. 3. In some embodiments, the view category that is associated with the at least one echocardiographic image may be associated with a function which can be applied to the at least one echocardiographic image to assess the quality of the at least one echocardiographic image. For example, in some embodiments, different analyses may be applied to a set of echocardiographic images, depending on which view category set of echocardiographic images falls within.

In some embodiments, the view categories with which the echocardiographic images may be associated may be chosen from a plurality of standard view categories. For example, the standard view categories may include the following 2D echocardiographic imaging plane views: AP2 (apical 2-chamber view), AP3 (apical 3-chamber view), AP4 (apical 4-chamber view), $PSAX_A$ (parasternal short axis at aortic valve level view) and $PSAX_{PM}$ (parasternal short axis at papillary muscle level view). In various embodiments, the standard view categories may include further or alternative view categories, such as, for example, any or all of the following 2D echocardiographic imaging plane view categories: parasternal long axis (PLAX), apical 5 chamber (AP5), subcostal view, aortic arch, or right parasternal. In various embodiments, with any of these views, an operator may switch the system 10 to Doppler and obtain 2D Color Doppler or Power Doppler, Continuous Wave Doppler and Duplex Doppler. In various embodiments, each view category may be associated with a different function for assessing quality of images.

In some embodiments, the block 204 may direct the analyzer processor 100 to determine which of the plurality of predetermined view categories the at least one echocardiographic image falls within before associating the image with the view category.

Figure 5:
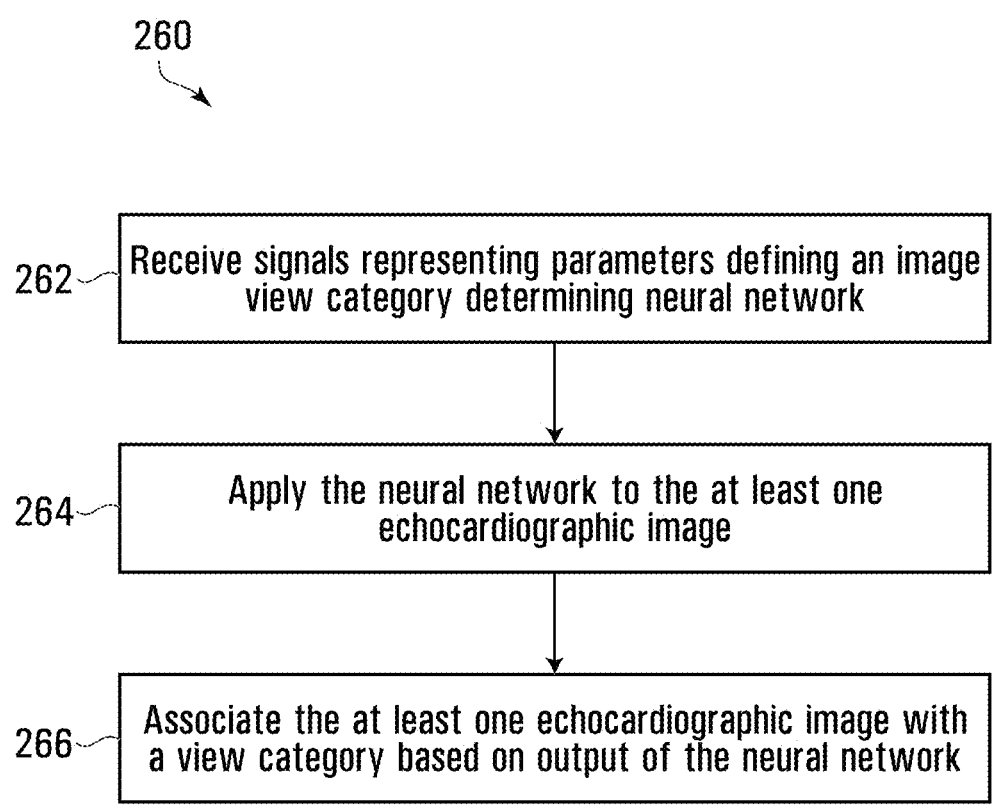
FIG. 5 is a flowchart depicting blocks of code that may be included in the flowchart of FIG. 3 in accordance with various embodiments of the invention.

For example, in some embodiments, this determination may be made automatically, such as by applying a function to the received at least one echocardiographic image. Referring to FIG. 5, there is shown at 260 a flowchart representing blocks of codes which may be included in the block 204 of the flowchart 200 shown in FIG. 3, in accordance with various embodiments. The blocks of codes included in the flowchart 260 may direct the analyzer processor 100 to apply one or more view categorization functions to the at least one echocardiographic image received at block 202 to determine which of a plurality of predetermined view categories the at least one echocardiographic image falls within.

Referring to FIG. 5, the flowchart 260 begins with block 262 which directs the analyzer processor 100 to receive signals representing parameters defining an image view category determining neural network. The image view category determining neural network may be configured to take the at least one echocardiographic images received at block 202 as an input and to output an indication of what image view category should be associated with the input at least one echocardiographic image.

Block 262 may direct the analyzer processor 100 to receive parameters defining the image view category determining neural network from the location 144 of the storage memory shown in FIG. 2, for example. The parameters defining the view category determining neural network may have been previously determined during training of the neural network and stored in the location 144 of the storage memory 104.

In some embodiments, a neural network trainer (for example, as shown at 502 in FIG. 14) may have previously determined architecture and weight and bias values for the view category determining neural network. Blocks of code included in the block of codes 160 of the program memory 102 may have previously directed the analyzer processor 100 to receive signals representing the architecture and weight and bias values via the interface 124 of the I/O interface 112 and to store a view category neural network record representing the architecture and the weight and the bias values in the location 144 of the storage memory 104.

Figure 6:
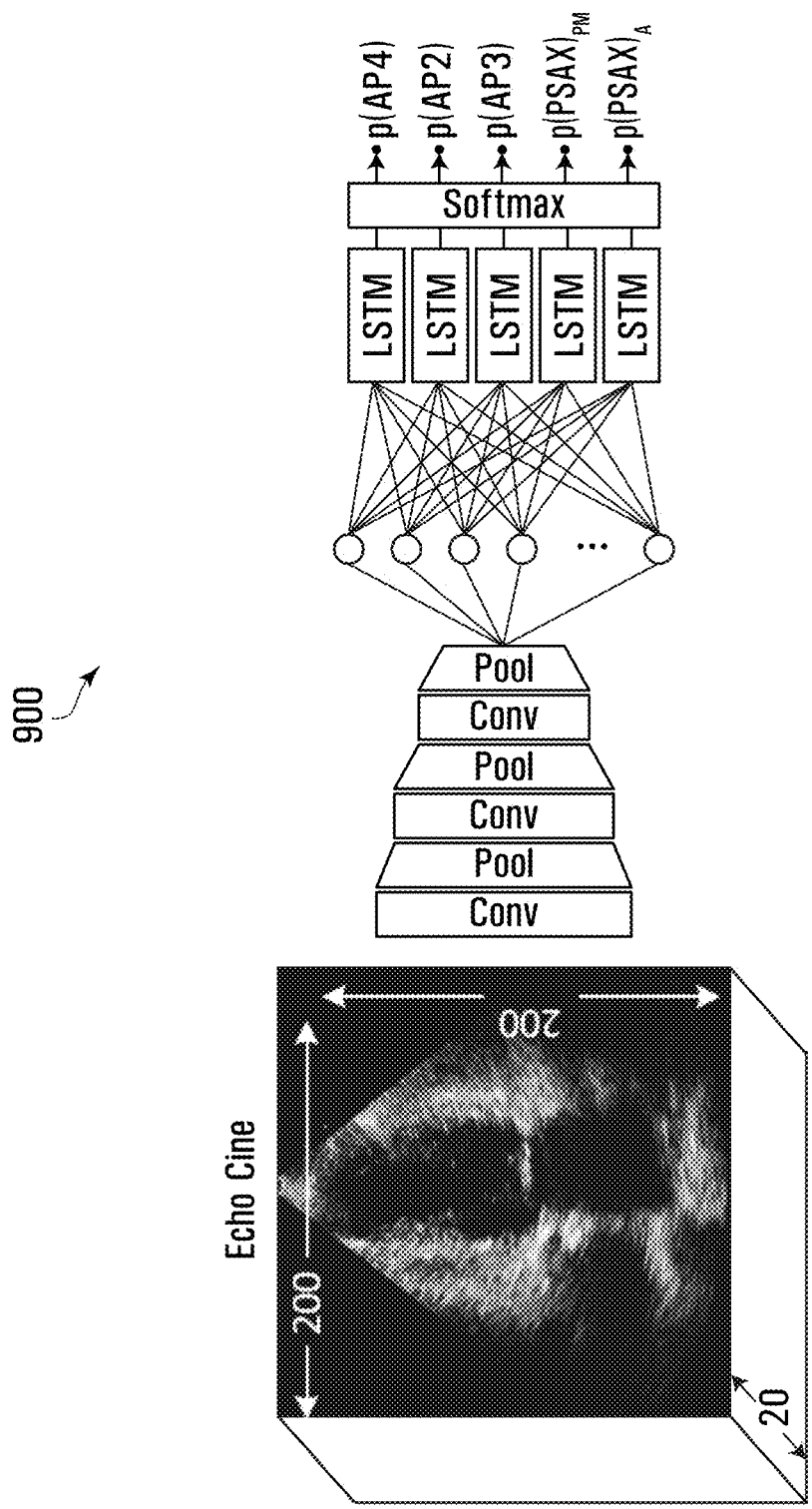
FIG. 6 is a representation of an exemplary view category determining neural network that may be used in the system shown in FIG. 1.

In some embodiments, the view category neural network record stored in the location 144 of the storage memory may represent a neural network having convolutional layers, max-pooling layers, one or more fully connected layers, one or more Long Short Term Memory (LSTM) layers, and a softmax layer acting as an output layer and having outputs which represent a likelihood that an input set of echocardiographic images falls within a particular view category. In some embodiments, the softmax outputs may indicate whether a set of echocardiographic images falls within one of the following standard 2D echocardiographic views, for example: AP2, AP3, AP4, $PSAX_A$, or $PSAX_{PM}$. An exemplary view category determining neural network that may be represented by the view category neural network record stored in the location 144 of the storage memory, in accordance with some embodiments, is shown at 900 in FIG. 6. The view category determining neural network takes as input, a sequence of 20 echocardiographic images, and outputs respective indicators that represent respective likelihoods that an input sequence of 20 echocardiographic images fall within a particular view category.

Referring back to FIG. 5, block 264 of the flowchart 260 then directs the analyzer processor 100 to apply the view category determining neural network defined by the parameters received at block 262 to the at least one echocardiographic image received at block 202 of the flowchart 200 shown in FIG. 3. Block 264 may direct the analyzer processor 100 to use the image data fields 244 of the 20 image files stored in the location 140 of the storage memory 104 at block 202 as input data for the view category determining neural network defined by the view category neural network record taken from the location 144 of the storage memory 104.

In some embodiments, the output of the neural network may be a softmax output which provides respective indicator values representing whether the set of images received at block 202 are AP2, AP3, AP4, PSAXA, and PSAXPM. In one embodiment, these indicator values may be 0.11, 0.05, 0.7, 0.11, 0.03, respectively, for example. In various embodiments, although the indicator values sum to 1.00, these values may not represent true probabilities that the at least one image received is of a particular view, as there may be a possibility that the at least one image is none of the views.

In some embodiments, block 264 of the flowchart 260 shown in FIG. 5 may direct the analyzer processor 100 to use a GPU included in the analyzer processor 100 to perform the neural network calculations. In some embodiments, use of the GPU instead of a general CPU may reduce the execution time for block 264.

Referring to FIG. 5, block 266 of the flowchart 260 then directs the analyzer processor 100 to associate the at least one echocardiographic image received at block 202 of the flowchart 200 shown in FIG. 3 with a view category based on the output of the neural network. In some embodiments, block 266 may direct the analyzer processor 100 to associate the at least one echocardiographic image with a view category that corresponds to the highest softmax output determined at block 264 of the flowchart 260 shown in FIG. 5. For example, with a softmax output which provides respective indicators for AP2, AP3, AP4, $PSAX_A$, and $PSAX_{PM}$ of 0.11, 0.05, 0.7, 0.11, 0.03, block 266 may direct the analyzer processor 100 to determine which output is the largest (i.e., the AP4 view category output) and to associate the images with that output.

Block 266 may direct the analyzer processor 100 to associate the at least one echocardiographic image received at block 202 of the flowchart 200 shown in FIG. 3 with the AP4 view category by generating a view category record 300 as shown in FIG. 7 and storing the view category record 300 in the location 142 of the storage memory 104. Referring to FIG. 7, the view category record 300 includes a view category identifier field 302 for storing an identifier for identifying the view category to be associated with the echocardiographic images and an image group identifier field 304 for storing an identifier for identifying the images with which the view category is to be associated.

In some embodiments, block 204 of the flowchart 200 shown in FIG. 3 may not include the blocks depicted in the flowchart 260, but rather an operator of the system 10 shown in FIG. 1 may input a view category by which the operator wishes to have the received echocardiographic images assessed. For example, in some embodiments, the operator may input a desired view category using an input device such as a keyboard and/or pointer or mouse of the user interface system 14. In such embodiments, block 204 may direct the analyzer processor 100 to receive operator input representing the view category via the interface 122 of the I/O interface 112 shown in FIG. 2. Block 204 may direct the analyzer processor 100 to, in response to receiving the input, generate and store a view category record in the location 142 of the storage memory 104 associating the received at least one echocardiographic image with the view category that the operator provided as input.

Referring back to FIG. 3, after block 204 has been executed, the at least one echocardiographic image received at block 202 may now be associated with a view category.

The flowchart 200 continues at block 206, which directs the analyzer processor 100 to determine, based on the at least one echocardiographic image received at block 202 and the view category associated with the echocardiographic image, a quality assessment value representing a view category specific quality assessment of the at least one echocardiographic image.

In some embodiments, each of the view categories may be associated with a function which can be applied by the analyzer to the received at least one echocardiographic image to generate the quality assessment value. In some embodiments, block 206 may direct the analyzer processor 100 to select a function to apply to the at least one echocardiographic image based on the view category associated with the received at least one echocardiographic image.

In various embodiments, applying the function may involve applying a neural network to the at least one echocardiographic image. A neural network is a non-linear model and so, in some embodiments, by using a neural network to analyze the echocardiographic images, the analyzer 12 may facilitate better functioning, for example, when there is variability in the echocardiographic image data than may be possible when analysis of the echocardiographic image relies on an average template or atlas with average shape.

Referring to FIG. 2, in various embodiments, a plurality of sets of parameters, each set defining a neural network, may be stored in the location 146 of the storage memory 104 shown in FIG. 2 and each of the sets of parameters may be associated with a view category to indicate that the set of parameters defines a neural network that is to be applied to echocardiographic images which are associated with that view category.

In some embodiments, the parameters may define neural network architectures and may include weight and bias values for the neural networks. A neural network trainer (for example, as shown at 502 in FIG. 14) may have previously determined the neural network architecture and/or the weight and bias values for each of the neural networks and provided these values to the analyzer 12. Blocks of code included in the block of codes 160 of the program memory 102 may have previously directed the analyzer processor 100 to receive signals representing the neural network architecture and the weight and bias values via the interface 124 of the I/O interface 112, for example, and to store this information in image assessment neural network records in the location 146 of the storage memory 104.

Figure 8:
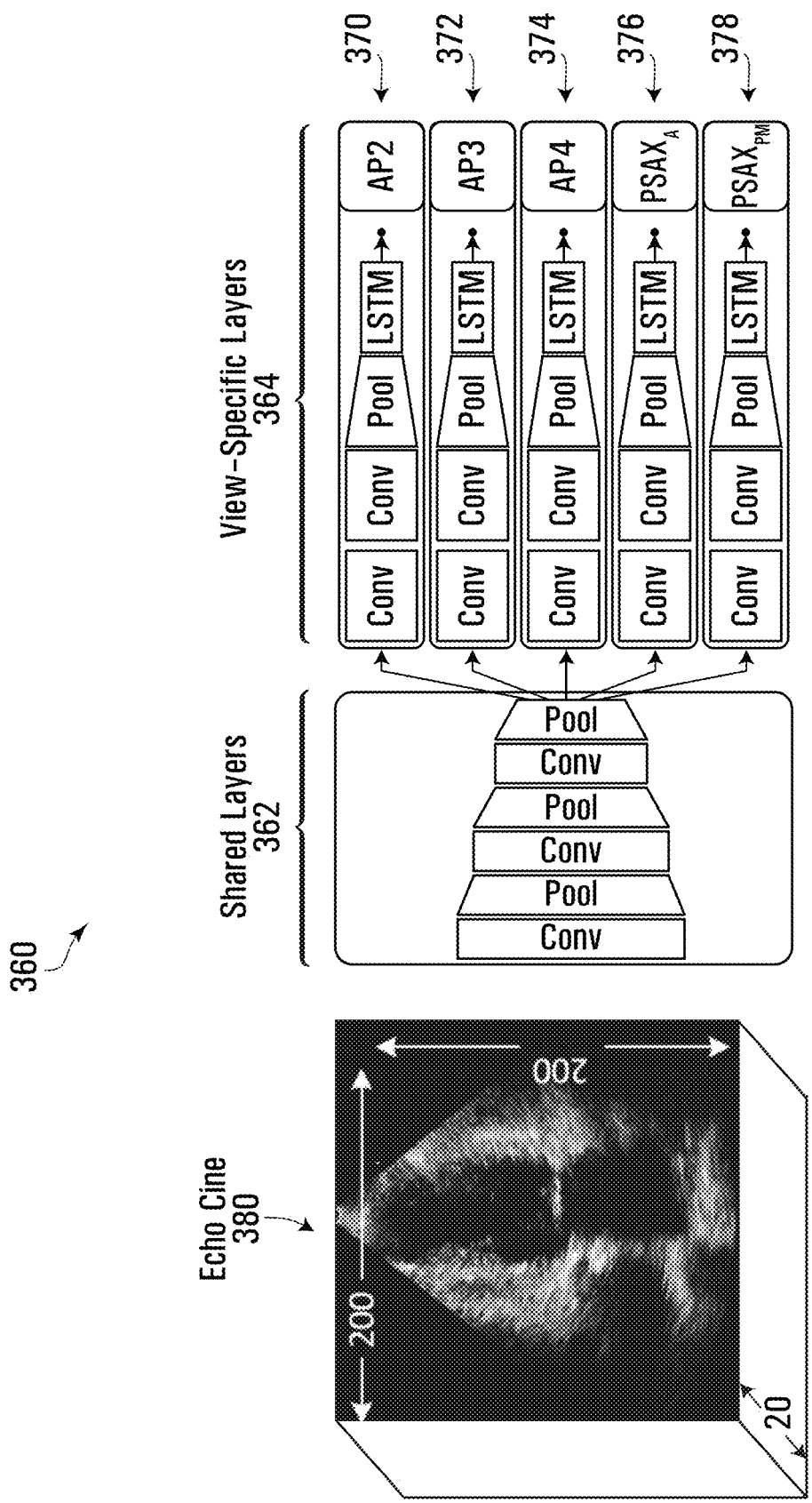
FIG. 8 is a representation of an exemplary image quality assessment neural network that may be used in the system shown in FIG. 1.

For example, in some embodiments, the image assessment neural network records stored in the location 146 of the storage memory 104 may represent the neural network shown at 360 in FIG. 8. Referring to FIG. 8, the neural network 360 includes 5 image quality assessment neural networks, each including the same shared layers 362 but including a different set of view category specific layers 370, 372, 374, 376, and 378. In various embodiments, the shared layers 362 and the view category specific layers 370, 372, 374, 376, and 378 may each be considered neural networks and it will be understood that a neural network may include more than one neural network within. Each of the 5 image quality assessment neural networks takes as an input a sequence of 20 echocardiographic images 380 and outputs a view category specific quality assessment value.

The neural network 360 shown in FIG. 8 is a deep neural network and a regression model, consisting of convolutional (cony), pooling (pool), and Long Short Term Memory (LSTM) layers, and in various embodiments, may be simultaneously trained to estimate the quality of a sequence of 20 echocardiographic images for any of five standard 2D echocardiographic views, AP2, AP3, AP4, $PSAX_A$, and $PSAX_{PM}$ by generating respective view category specific quality assessment values.

The neural network architecture, depicted in FIG. 8, represents a multi-stream network, i.e., five regression models that share weights across the first few common shared layers 362. Each stream of the network has its own view-specific layer 370, 372, 374, 376, and 378 and has been trained based on the mean absolute error loss function, via a stochastic gradient-based optimization algorithm, to minimize the absolute difference between normalized quality assessment values assigned by a trained echocardiographer to training images, as discussed further below, and the generated quality assessment values.

In the embodiment shown, all cony layers have kernels with the size of 3×3, which may, for example, follow the VGG architecture discussed in Simonyan, K., Zisserman, A.: Very Deep Convolutional Networks for Large-Scale Image Recognition. International Conference on Learning Representations (ICRL) pp. 1-14 (2015), with the number of kernels doubling for deeper cony layers, i.e., from 8 to 32 kernels. In some embodiments, the cony layers may extract hierarchical features in the image, with the first three shared layers 362 modeling high level spatial correlations, and the next two cony layers of the view category specific layers 364 focusing on view-specific quality features. In some embodiments, activation functions of the cony layers may be Rectified Linear Units (ReLUs).

Referring still to FIG. 8, in various embodiments, the pool layers of the neural network 360 may be 2×2 max-pooling with a stride of 2 to facilitate selection of superior invariant features and divide the input feature-map size in half in both dimensions to reduce feature variance and train more generalized models. The cony and pool layers are applied to each image of an input echo cine, independently.

The output feature map of the last pool layer is flattened and sent to an LSTM unit, a type of Recurrent Neural Networks (RNN) that uses a gated technique to selectively add or remove information from the cell state. Each set of view category specific layers 370, 372, 374, 376, and 378 in the neural network 360 shown in FIG. 8 uses a single LSTM cell to analyze 20 feature-sets corresponding to the 20 consecutive input images. The LSTM layer uses hard sigmoid functions for inner and output activations.

In some embodiments, the image assessment neural network records stored in the location 146 of the storage memory 104 which represent the neural network 360 may include a common neural network record representing the shared layers 362 and a plurality of different view category specific neural network records representing the sets of view category specific layers 370, 372, 374, 376, and 378.

A representation of a portion of an exemplary common neural network record for storing a set of parameters defining the shared layers 362 of the neural network 360 shown in FIG. 8, is shown at 320 in FIG. 9. Referring to FIG. 9, the common neural network record 320 includes first, second, third, fourth, fifth and sixth sets of fields 324, 326, 328, 330, 332, and 334 defining the parameters for the six layers of the shared layers 362 of the neural network 360 shown in FIG. 8. For ease of reference, not all kernel fields of the common neural network record 320 are shown in FIG. 9 and the content of the kernels is shown as [ . . . ], though it will be understood that there are 8 kernels in layer 1, 16 kernels in layer 3 and 32 kernels in layer 5 and that each kernel field stores a 3×3 matrix of values.

Figure 10:
FIG. 10 is a representation of an exemplary view category specific neural network record that may be used in the system shown in FIG. 1.

A representation of a portion of an exemplary view category specific neural network record for storing a set of parameters defining the set of view category specific layers 374 of the neural network 360 shown in FIG. 8, is shown at 340 in FIG. 10. Referring to FIG. 10, the view category specific neural network record 340 includes a view category identifier field 342 for storing a view category identifier identifying which view category the record is associated with and seventh, eighth, ninth, and tenth sets of fields 344, 346, 348, and 350 for storing parameters defining the set of view category specific layers 374 of the neural network 360 shown in FIG. 8. For ease of reference, not all kernel fields are shown in FIG. 10 and the content of the kernels and LSTM parameters are shown as [ . . . ], though it will be understood that there are 32 kernels in layer 7 and 32 kernels in layer 9 and that each kernel field stores a 3×3 matrix of values and the LSTM parameter fields store values defining the parameters of the LSTM.

Additional neural network records representing the sets of shared layers 370, 372, 376 and 378 having generally the same format as the view category specific neural network record 340 shown in FIG. 10 may also be stored in the location 146 of the storage memory 104. Thus, each of the image view categories AP2, AP3, AP4, $PSAX_A$, and $PSAX_{PM}$ may be associated with a view category specific neural network record stored in the location 146 of the storage memory 104.

In various embodiments, splitting the neural network 360 into a common portion and view category specific portions may facilitate more efficient training of the neural networks. In some embodiments, splitting the neural network 360 into a common portion and view category specific portions may result in requiring fewer learning parameters than would be required if using fully separate neural networks, which may help facilitate easier transferring of a neural network to a new machine, and/or may reduce memory usage.

Figure 11:
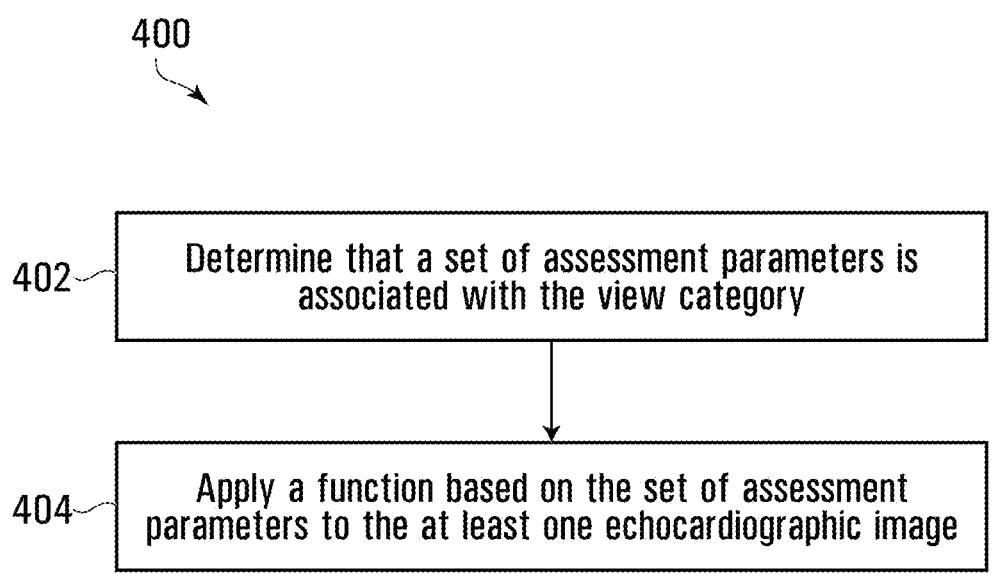
FIG. 11 is a flowchart depicting blocks of code that may be included in the flowchart of FIG. 3 in accordance with various embodiments of the invention.

Referring now to FIG. 11, there is shown at 400 a flowchart representing blocks of codes which may be included in the block 206 of the flowchart 200 shown in FIG. 3, in accordance with various embodiments. The blocks included in the flowchart 400 may direct the analyzer processor 100 to determine which of the sets of quality assessment parameters is associated with the same view category as the at least one echocardiographic image received at block 202 and to apply a function based on that set of quality assessment parameters.

The flowchart 400 begins with block 402 which directs the analyzer processor 100 to determine that a set of assessment parameters of the sets of assessment parameters stored in the location 146 is associated with the same view category that is associated with the at least one echocardiographic image received at block 202.

For example, in some embodiments, block 402 may direct the analyzer processor 100 to read "AP4" from the view category identifier field 302 of the view category record 300 associated with the echocardiographic image files received at block 202. Block 402 may direct the analyzer processor 100 to read the view category specific neural network records from the location 146 of the storage memory to find a view category specific neural network record that includes the same view category identifier of "AP4" and is therefore associated with the same view category. Accordingly, block 402 may direct the analyzer processor 100 to determine that the view category specific neural network record 340 includes the view category identifier of "AP4" and is therefore associated with the same view category that is associated with the at least one echocardiographic image received at block 202.

Block 404 then directs the analyzer processor 100 to, in response to determining that the set of assessment parameters is associated with the same view category, apply a function based on the set of assessment parameters to the at least one echocardiographic image received at block 202. In some embodiments, block 404 may direct the analyzer processor 100 to apply the neural network defined by the parameters included in the common neural network record 320 and the view category specific neural network record 340 to the image data in the image files received at block 202.

Block 404 may direct the analyzer processor 100 to read the image files received at block 202 from the location 140 of the storage memory 104 and to read the common neural network record 320 and the view category specific neural network record 340 from the location 146 of the storage memory, and to input the image data from the image files into a neural network that includes the shared layers 362 and the view category specific layers 374 shown in FIG. 8, which are defined by the common neural network record 320 and the view category specific neural network record 340, to generate or determine a view category specific quality assessment value as an output of the neural network.

In some embodiments, the quality assessment value may represent a suitability for a quantified clinical measurement. In some embodiments, the quality assessment value may represent an estimate of an expected score which would be provided by an expert to the input at least one echocardiographic image. The estimate may be based on the training of the neural network wherein an expert provided quality assessment values for various echocardiographic images.

In some embodiments, the quality assessment value may be a score with criteria and/or a range that varies depending on the view category with which the neural network is associated. In some embodiments, the expert which provided the quality assessment values with which the neural network was trained may have determined the quality assessment values as an aggregation of scores derived using semi-quantitative evaluation of component structures and parameter optimization features such as centering, depth, gain, axis, focus, frequency or another parameter optimization feature or image capture parameter. Accordingly, in various embodiments, the quality assessment value may represent an estimate of an expected aggregation of scores derived using semi-quantitative evaluation of component structures and parameter optimization features such as centering, depth, gain, axis, focus, frequency or another parameter optimization feature or image capture parameter.

For example, in some embodiments, an expert may have, for each at least one echocardiographic image that they assessed, determined for each component in the at least one echocardiographic image, a component quality score of up to 2 points based on the following observations: 0 points) the structure was not imaged or was inadequate for assessment; 1 point) the structure was adequately viewed; 2 points) the view was optimized for the structure. In some embodiments, the component score may act as a clinical plane assessment value representing an expert opinion whether the associated echocardiographic training image was taken in an anatomical plane suitable for a quantified clinical measurement of anatomical features. The expert may have, for each at least one echocardiographic image that they assessed, determined parameter optimization scores as follows: appropriate centering (1 point), correct depth setting (0.5 points), proper gain (0.5 points), correct axis (1 point), and correct depth of focus (0.5 points). In various embodiments, the quality assessment value may represent a sum of the above-noted scores.

As discussed above, in some embodiments, images for the different view categories may include a different set of components and quality assessment values may be determined using different criteria. For example, for the AP2 view category, the left ventricle (LV), left atrium (LA), and mitral valve (MV) may each be assigned a component quality score, which may be summed with scores for centering, depth, and gain to determine the quality assessment value. For the AP3 view category, the aortic valve (AV), MV, LA, LV, and septum may each be assigned a component quality score, which may be summed with scores for centering, depth, and gain to determine the quality assessment value. For the AP4 view category, the LV, right ventricle (RV), LA, right atrium (RA), MV, and TV may each be assigned a component quality score, which may be summed with scores for centering, depth, and gain to determine the quality assessment value. For the $PSAX_A$ view category, the AV and leaflets may each be assigned a component quality score, which may be summed with scores for centering, depth, and gain to determine the quality assessment value. For the $PLAX_{PM}$ the papillary muscles may be assigned a component quality score, which may be summed with scores for centering, depth, gain, and axis to determine the quality assessment value.

In some embodiments, the quality assessment values for all views may be normalized to the same scale, which may be, for example, between 0 and 1 or between 0 and 5.

Referring back to FIG. 11, in some embodiments, block 404 of the flowchart 400 may direct the analyzer processor 100 to apply the neural network such that the quality assessment value and associated at least one echocardiographic image may be viewed in real-time or near-real time for the operator. For example, in some embodiments, block 404 may direct the analyzer processor 100 to apply the neural network and determine a quality assessment value in less than about 3 seconds. In some embodiments, block 404 may direct the analyzer processor 100 to apply the neural network and determine a quality assessment value in less than about 1 second. In some embodiments, block 404 may direct the analyzer processor 100 to apply the neural network and determine a quality assessment value in less than about 0.33 ms. In some embodiments, for an input echo cine of 20 images of 200×200 pixels, a quality assessment value may be determined in about 10 ms, which may be suitable for real-time or near real-time deployment. In some embodiments, block 404 may direct the analyzer processor 100 to use a GPU included in the analyzer processor 100 to apply the neural network. In some embodiments, use of the GPU instead of just a general CPU may reduce the time it takes to execute the block 404 and may thus facilitate real-time or near-real time image analysis.

Referring back to FIG. 3, the flowchart 200 continues at block 208 which directs the analyzer processor 100 to produce signals representing the quality assessment value determined at block 206, for causing the quality assessment value to be associated with the at least one echocardiographic image received at block 202.

In some embodiments, block 208 may direct the analyzer processor 100 to produce signals for causing the quality assessment value to be stored in the location 148 of the storage memory 104. For example, in some embodiments, block 208 may direct the analyzer processor 100 to store a quality assessment record 420 as shown in FIG. 12 in the location 148 of the storage memory 104, wherein the quality assessment record 420 includes an image group identifier field 422 for storing the group identifier which identifies the group of images for which the quality assessment was made and a quality assessment value field 424 for storing the quality assessment that was generated at block 404 of the flowchart 400.

In some embodiments, block 208 may direct the analyzer processor 100 to produce signals for causing a representation of the quality assessment value to be transmitted to the display 15 of the user interface system 14 for causing the display to display the quality assessment value in association with the received at least one echocardiographic image. In some embodiments, this may assist one or more operators of the system 10 in capturing subsequent echocardiographic images. For example, in some embodiments, block 208 may direct the analyzer processor 100 to communicate with the user interface system 14 of the system 10 shown in FIG. 1 via the interface 122 of the I/O interface 112 shown in FIG. 2 to cause a display 440 as shown in FIG. 13 to be presented on the display 15 of the user interface system 14.

Figure 13:
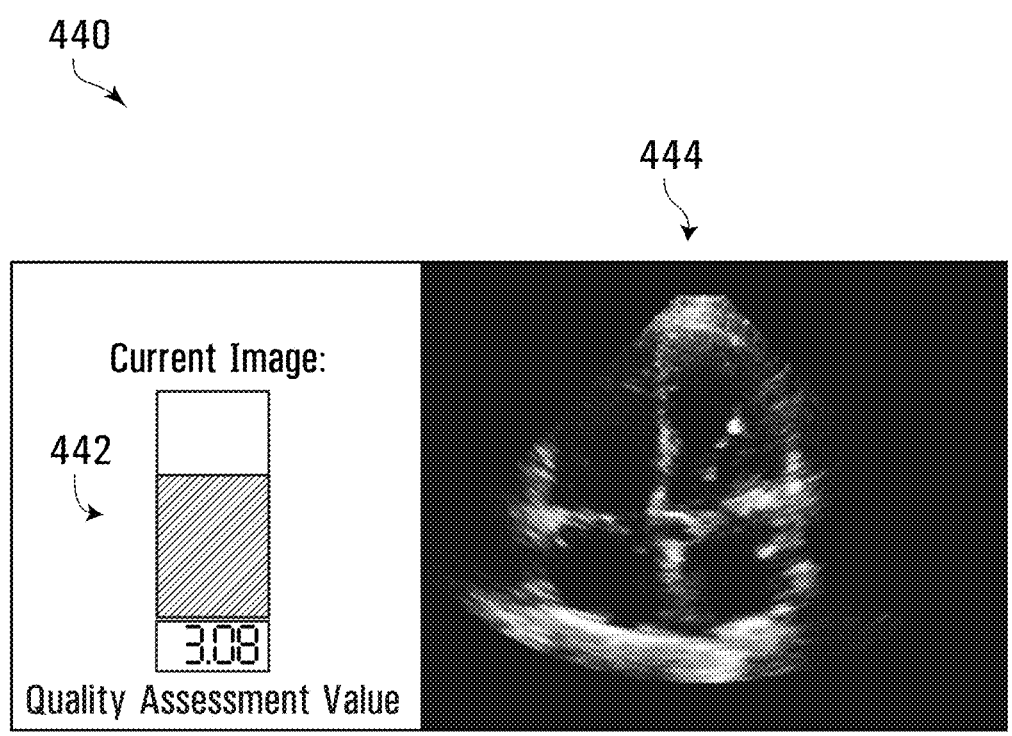
FIG. 13 is a representation of a display that may be presented by a display of a user interface system included in the system shown in FIG. 1 in accordance with embodiments of the invention.

Referring to FIG. 13, the display 440 includes a representation 442 of the quality assessment value determined at block 206 shown in association with a representation 444 of the at least one echocardiographic image received at block 202.

In some embodiments, block 208 may direct the analyzer processor 100 to transmit the quality assessment value and associated at least one echocardiographic image to another device for storage and/or further analysis. For example, in various embodiments, block 208 may direct the analyzer processor 100 to transmit a representation of the image files stored at block 202 and the quality assessment record generated at block 208 to an archive device in a picture archiving and communication system (PACS) via the interface 124 and the network 126, for example.

In various embodiments, once block 208 has been executed, the analyzer processor 100 may be directed to return to block 202 to receive further echocardiographic images. In some embodiments, the flowchart 200 may be executed continuously such that the display 440 shown in FIG. 13 is updated with near real-time updates of images or image sequences and associated quality assessment values. In some embodiments, an operator may adjust image capture parameters of the system 10 and/or adjust positioning of the transducer until the operator sees a desired quality assessment value.

In some embodiments, the operator may make adjustments until a quality assessment value of greater than a predetermined threshold value is achieved. In some embodiments, for example, where the quality assessment value has been normalized to a possible range of 0-5 the threshold value may be about 3.0.

In some embodiments, there may be a maximum achievable quality assessment value for a given patient and the maximum achievable quality assessment value may be dependent on the patient, given their anatomy and/or echogenicity, for example. For example, in some embodiments where the quality assessment value has been normalized to a possible range of 0-5, for many patients, the maximum achievable quality assessment value for a given view category may be about 3.0. In some embodiments, the operator may make various adjustments until a near maximum achievable quality assessment value on a given patient has been achieved.

In some embodiments, after capturing images associated with a desired quality assessment value for a first view category, the operator of the system 10 may wish to capture images for a different view category and so reposition the transducer and/or reconfigure the system 10. For example, in some embodiments, the operator may, after capturing images of the AP4 view category, wish to capture images of one or more of the AP2, AP3, $PSAX_A$, and $PSAX_{PM}$ view categories to facilitate quantified clinical measurement of anatomical features and/or to assist in diagnosing a medical condition or a characteristic of the heart. For example, in some embodiments, the operator may, after capturing at least one image of the AP4 view category, wish to capture at least one image of the AP2 view category to facilitate quantified clinical measurement of anatomical features for determining an ejection fraction.

Accordingly, the operator may reposition the transducer 16 shown in FIG. 1 and/or adjust image receiving parameters to cause the flowchart 200 to be executed one or more further times, but with echocardiographic images which are of different view categories and are to be analyzed using different parameters. In various embodiments, the analyzer 12 being configured as described above to switch between analyses of varying view categories may facilitate ease of use and/or efficient capture of subsequent high quality images of different view categories.

Neural Network Trainer

Figure 14:
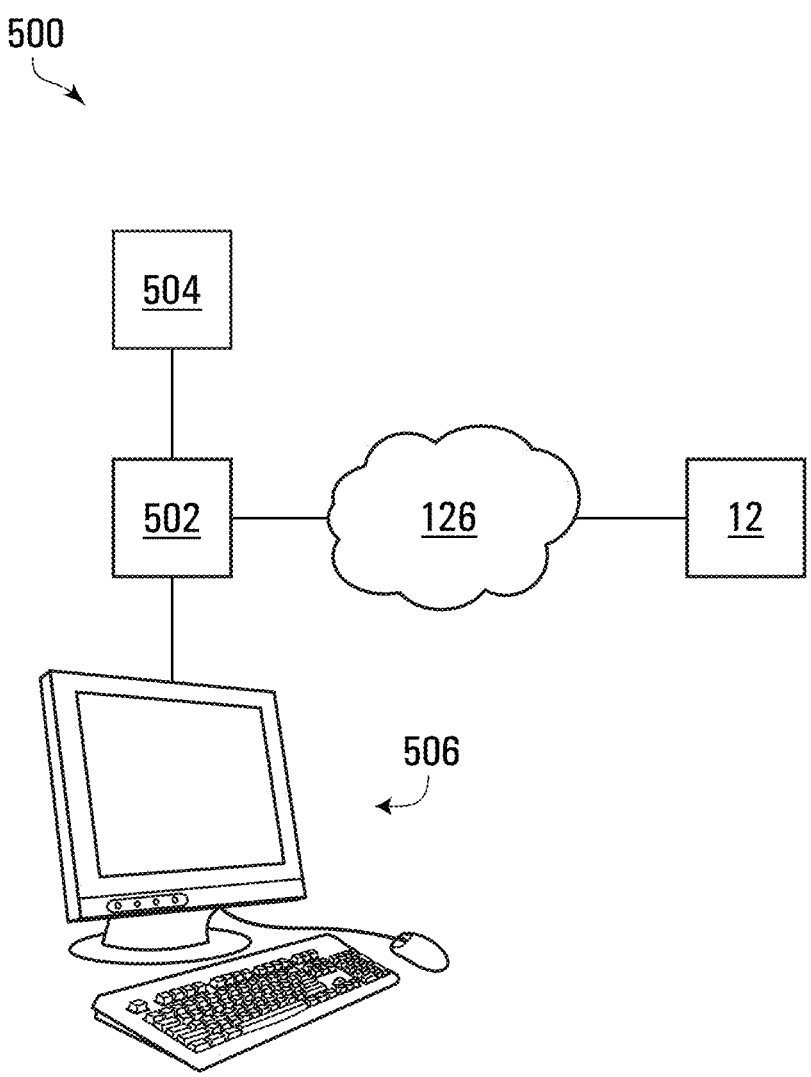
FIG. 14 is a schematic view of a system for training neural networks to facilitate echocardiographic image analysis in accordance with various embodiments of the invention.

As discussed above, in various embodiments, a neural network trainer may first train neural networks to determine the architecture and/or parameters to be used by the neural networks at block 204 and/or block 206 of the flowchart 200 shown in FIG. 3. Referring to FIG. 14, there is shown a system 500 for facilitating training of neural networks. The system includes a neural network trainer 502 in communication with a training image source 504 and a user interface system 506. In some embodiments, the neural network trainer 502 may also be in communication with the analyzer 12 via the network 126.

The training image source 504 stores echocardiographic images and associated view category information which indicates what view category each of the images falls within. For example, in some embodiments, the training image source 504 may include a server computer for storing and archiving medical electronic images, such as, for example, an archive device from a picture archiving and communication system (PACS).

The neural network trainer 502 may be configured to retrieve and/or receive the echocardiographic images, which may act as echocardiographic training images, from the training image source 504. In some embodiments, the neural network trainer 502 may, after receiving the training images, produce signals representing the echocardiographic training images and associated view categories to cause the user interface system 506 to present the echocardiographic images and the view categories to one or more experts, such as, echocardiographers or physicians trained in echocardiography.

The experts may then provide respective quality assessment values for each of the echocardiographic images. For example, in some embodiments, the neural network trainer may be configured to produce signals for causing the user interface system 506 to present the experts with a set of echocardiographic training images and an indication of what view category the set of echocardiographic training images is to be assessed as. An echocardiographer may assess the set of echocardiographic training images and provide a quality assessment value representing a suitability of the set of images for a quantified clinical measurement. The neural network trainer 502 may store the quality assessment value in memory in association with the assessed set of echocardiographic training images.

After quality assessment values have been received and associated with each set of echocardiographic training images, the neural network trainer 502 may train neural networks using the echocardiographic training images as inputs and the associated expert quality assessment values as desired outputs to determine sets of neural network parameters defining the neural networks, wherein at least a portion of each of the neural networks is associated with one of the image view categories.

In some embodiments, the neural network trainer 502 may also train a view category determining neural network to determine sets of neural network parameters defining the view category determining neural network. The view category determining neural network may be generally as described above with reference to block 262 of the flowchart 260 shown in FIG. 5, configured to receive one or more echocardiographic images as an input, and having a softmax layer as an output layer having outputs which represent whether the input echocardiographic images fall within a particular view category.

In some embodiments, the neural network trainer 502 may produce signals representing the parameters defining the trained neural networks for causing the parameters to be provided to a system or device configured to apply the neural networks. For example, in some embodiments, the neural network trainer 502 may transmit the neural network parameters to the analyzer 12 via the network 126 shown in FIG. 14. Alternatively, in some embodiments, the neural network trainer 502 may produce signals for causing the sets of neural network parameters to be stored in removable memory which may be provided to the analyzer 12.

The analyzer 12 may use the sets of neural network parameters to facilitate analysis of echocardiographic images, generally as described above with reference to the flowchart 200 shown in FIG. 3.

Neural Network Trainer—Processor Circuit

Figure 15:
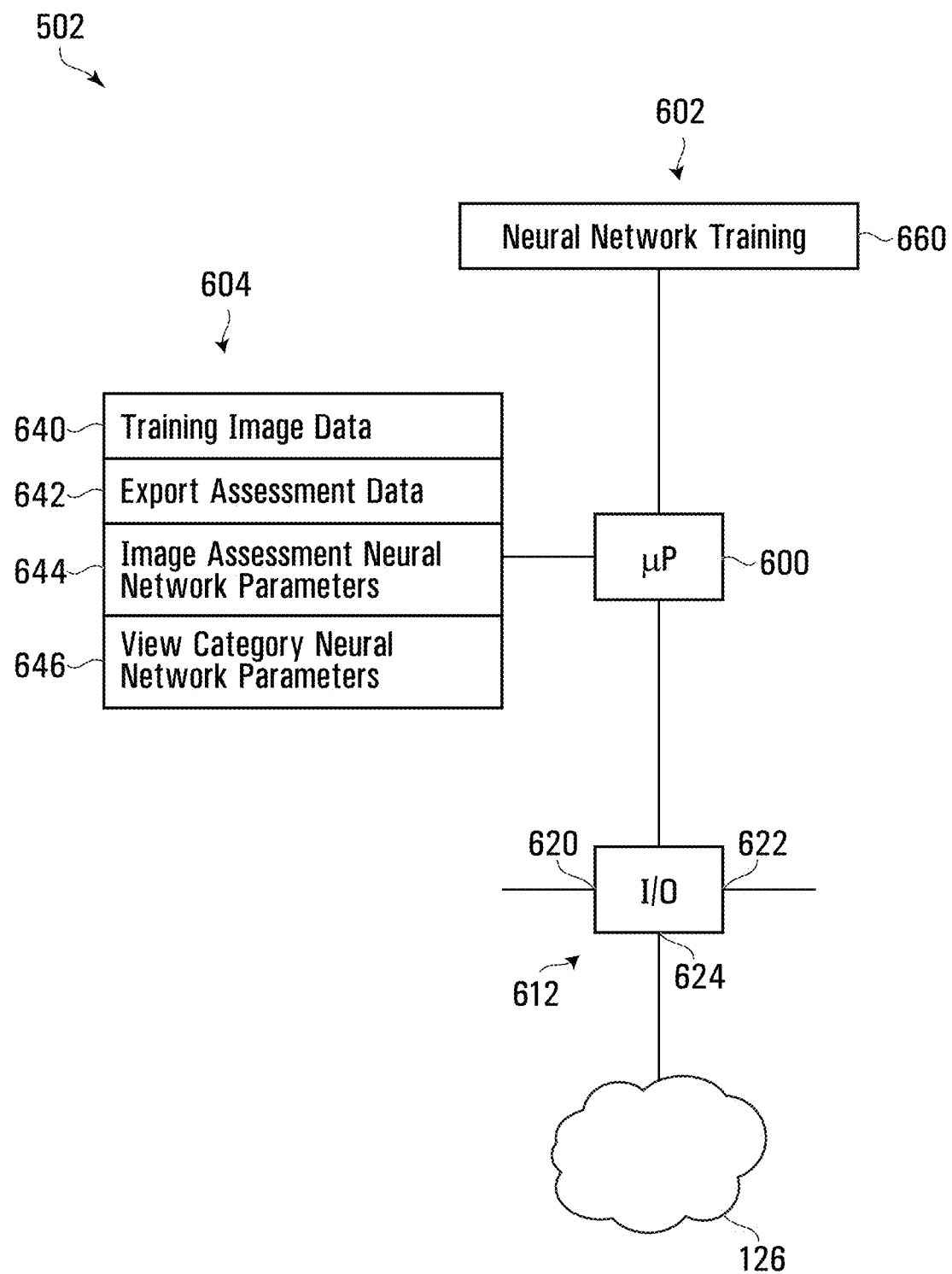
FIG. 15 is a schematic view of a neural network trainer of the system of FIG. 1 including a processor circuit in accordance with various embodiments of the invention.

Referring now to FIG. 15, a schematic view of the neural network trainer 502 of the system 500 shown in FIG. 14 according to an embodiment is shown. In various embodiments, the neural network trainer 502 may be incorporated in one or more computers, for example.

Referring to FIG. 15, the neural network trainer 502 includes a processor circuit including a trainer processor 600 and a program memory 602, a storage memory 604, and an I/O interface 612, all of which are in communication with the trainer processor 600.

The I/O interface 612 includes an interface 620 for communicating with the training image source 504 and an interface 622 for communicating with the user interface system 506 shown in FIG. 14. In some embodiments, the I/O interface 612 also includes an interface 624 for facilitating networked communication with the analyzer 12 through the network 126.

Processor-executable program codes for directing the trainer processor 600 to carry out various functions are stored in the program memory 602. The program memory 602 includes a block of codes 660 for directing the neural network trainer 502 to perform neural network training functions.

The storage memory 604 includes a plurality of storage locations including location 640 for storing training image data, location 642 for storing expert assessment data, location 644 for storing image assessment neural network parameter data and location 646 for storing view category neural network parameter data.

Training the Neural Networks

Figure 16:
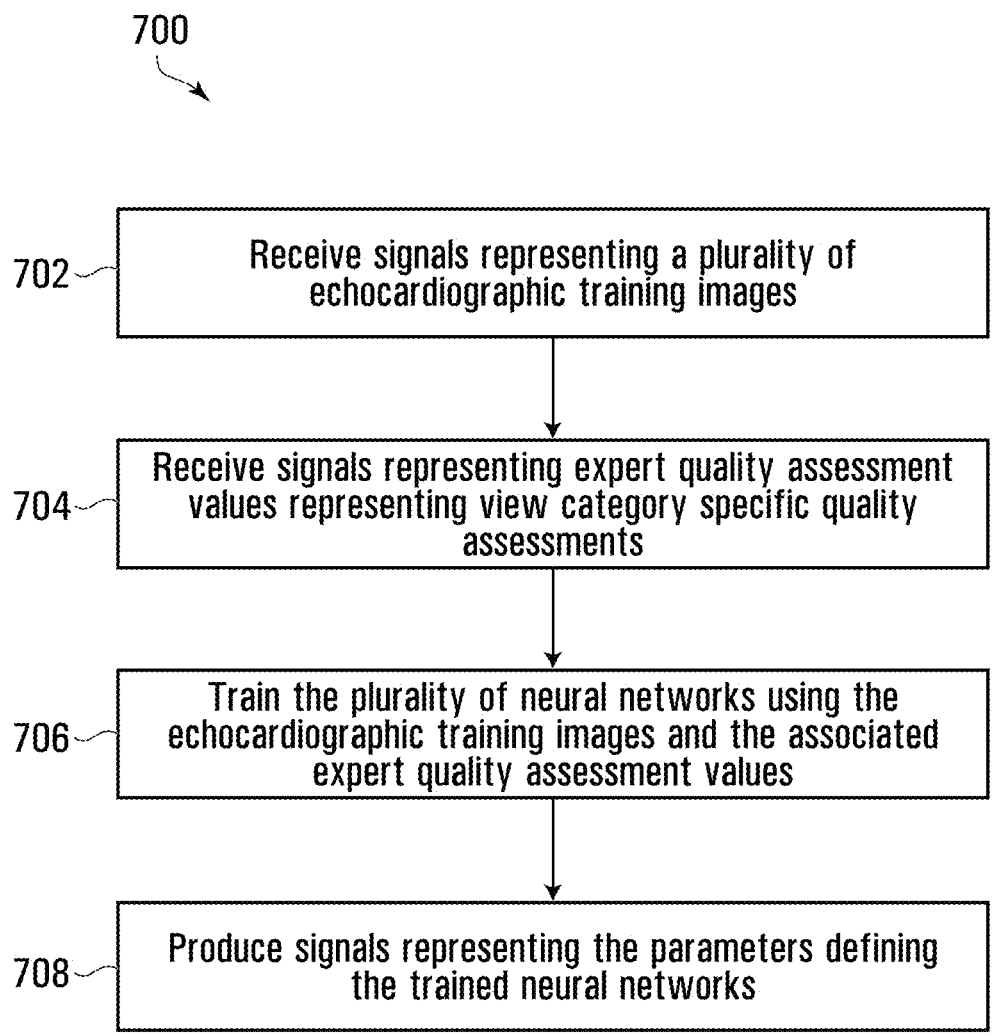
FIG. 16 is a flowchart depicting blocks of code for directing the trainer of the system of FIG. 14 to perform image assessment neural network training functions in accordance with various embodiments of the invention.

Referring now to FIG. 16, a flowchart depicting blocks of code for directing the trainer processor 600 shown in FIG. 15 to perform image assessment neural network training functions in accordance with one embodiment is shown generally at 700. The blocks of code included in the flowchart 700 may be encoded in the block of codes 660 of the program memory 602 shown in FIG. 15 for example.

Referring to FIG. 16, the flowchart 700 begins with block 702 which directs the trainer processor 600 shown in FIG. 15 to receive signals representing a plurality of echocardiographic training images, each of the plurality of echocardiographic training images associated with one of a plurality of predetermined echocardiographic image view categories. In some embodiments, block 702 may direct the trainer processor 600 to receive echocardiographic training images from the training image source 504 shown in FIG. 14. For example, in some embodiments, block 702 may direct the trainer processor 600 to receive sets of associated image files, which may represent respective sequences of images or videos and include common image group identifiers, from the training image source 504. Each set of image files may make up an echo cine, which is associated with a view category.

Figures 17, 18:
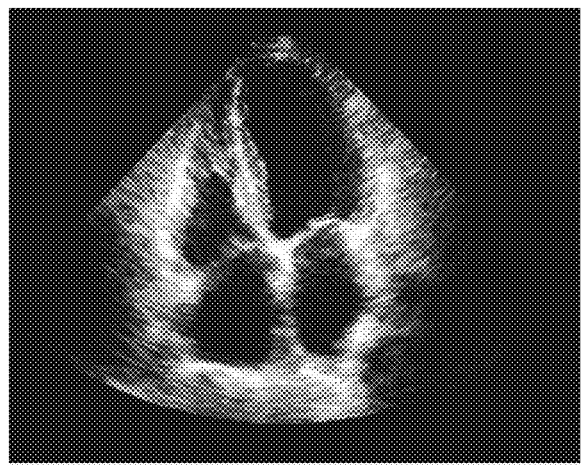
FIG. 17 is a representation of an exemplary training image file that may be used in the system shown in FIG. 1.
FIG. 18 is a representation of an exemplary expert quality assessment record that may be used in the system shown in FIG. 1.

An exemplary training image file that may be received at block 702 is shown at 740 in FIG. 17. The training image file 740 includes an image identifier field 742 for storing a unique identifier for identifying an image included in the file, an image group identifier field 744 for storing an identifier common to a set of image files which include images that are to be analyzed together, a view category identifier field 746 for storing an identifier for identifying the view category within which the image falls and by which the image should be analyzed, and an image data field 748 for storing information representing the image.

Block 702 may direct the trainer processor 600 to store the training image files received at block 702 in the location 640 of the storage memory 604.

After block 702 of the flowchart 700 shown in FIG. 16 has been executed, the location 640 of the storage memory 604 shown in FIG. 17 may store a large number of image files, each having generally similar format to the training image file 740 shown in FIG. 17. For example, in some embodiments, about 2,500 echo cines of about 40 images each (about 500 echo cines of each view category) may be stored in the location 640 of the storage memory 604 and therefore about 100,000 training image files generally similar to the training image file 740 shown in FIG. 17 may be stored in the location 640 of the storage memory 104.

Referring back to FIG. 16, block 704 directs the trainer processor 600 to receive signals representing expert quality assessment values representing view category specific quality assessments of the echocardiographic training images, each of the expert quality assessment values provided by an expert echocardiographer and associated with one of the received sets of echocardiographic training images.

In some embodiments, the neural network trainer 502 may cause the echocardiographic training images to be presented to an expert and the expert may provide the expert quality assessment values. For example, block 704 may direct the trainer processor 600 to transmit the training image files to the user interface system 506 via the interface 622 of the I/O interface 612 shown in FIG. 15 to cause a display of the user interface system 506 to present one or more experts with the echocardiographic images and an indication of what view category the images are to be assessed as.

In some embodiments, the echocardiographers may be directed to provide a quality assessment value representing a suitability of the images for a quantified clinical measurement. For example, the echocardiographers may be directed to provide a quality assessment value, which represents an aggregation of scores derived using semi-quantitative evaluation of component structures and parameter optimization features such as centering, depth, gain, axis, focus, frequency or another parameter optimization feature or image capture parameter, generally as described above, with reference to flowchart 400 shown in FIG. 11.

Block 704 may direct the trainer processor 600 to receive signals representing the expert quality assessment values and to store representations of the received expert quality assessment values in the location 642 of the storage memory 604. For example, in some embodiments, block 704 may direct the trainer processor 600 to receive representations of expert quality assessment records from the user interface system 506 and to store the expert quality assessment records in the location 642 of the storage memory. An exemplary expert quality assessment record that may be received at block 704 and stored in the location 642 of the storage memory 604 is shown at 780 in FIG. 18.

Referring to FIG. 18, the expert quality assessment record 780 includes an image group identifier field 782 for storing the group identifier which identifies the set of images for which the expert quality assessment was made and an expert quality assessment value field 784 for storing the view category specific expert quality assessment value provided by the expert.

Referring back to FIG. 16, the flowchart 700 continues at block 706 which directs the trainer processor 600 shown in FIG. 15 to train neural networks using the echocardiographic training images and the associated expert quality assessment values to determine sets of neural network parameters defining the neural networks, at least a portion of each of said neural networks associated with one of the plurality of predetermined echocardiographic image view categories.

In some embodiments, block 706 may direct the trainer processor 600 to train the neural network 360 shown in FIG. 8 to determine values to be included in a common neural network record and view category specific neural network records stored in the location 644 of the storage memory 104. In various embodiments, the common neural network record stored in the location 644 may have a generally similar format to that of the common neural network record 320 shown in FIG. 9 and each of the view category specific neural network records stored in the location 644 of the storage memory 604 may have a generally similar format to that of the view category specific neural network record 340 shown in FIG. 10.

In some embodiments, the sequences of images received at block 702 may include a different number of images than can be analyzed by the neural network to be applied. For example, in some embodiments, the neural network 360 shown in FIG. 8 may be configured to take as an input 20 images and the sequences of images received at block 702 may include more than 40 images each. Accordingly, in some embodiments, before training the neural networks, block 706 may direct the trainer processor 600 to split one or more groups of echocardiographic images received at block 702 into subsets.

For example, block 706 may direct the trainer processor 600 to split each sequence of images into one or more groups of 20 image files each. In order to do this, block 706 may direct the trainer processor 600 to change the value stored in the image group identifier field for each file. Block 706 may further direct the trainer processor 600 to generate and store further expert quality assessment records as necessary such that each of the new groups of images is associated with the same quality assessment value as the original sequence of images.

Due to the storage length of heart cycles and different frame acquisition rates, number of images per cardiac cycle may vary for different image sequences. Accordingly, in some embodiments the neural network may be defined to take as input a static sequence size of nearly half the average heart cycle in the echocardiographic images received at block 702 (for example, in some embodiments 20 images), to capture the quality distribution of the echo imaging view categories. In various embodiments, by choosing a static sequence size of about half the average heart cycle, images in each sequence may not be synced with the heart cycle and this may, in some embodiments, help to ensure that the estimated quality assessment value provided after training for a given input sequence may be independent of the starting phase of the cardiac data.

Block 706 may direct the trainer processor 600 to, for each 20 image sequence of images having a common group identifier value, select a set of layers of the neural network 360 shown in FIG. 8 to train, and to train those layers. For example, for a 20 image sequence associated with the AP4 view category, block 706 may direct the trainer processor 600 to train the neural network including the shared layers 362 and the AP4 view category specific layers 374. Block 706 may direct the trainer processor 600 to use the 20 images as inputs and to use the expert quality assessment value from an associated expert quality assessment record stored in the location 642 of the storage memory 604 as the desired output.

In some embodiments, block 706 may direct the trainer processor 600 work towards optimizing network hyper-parameters by cross-validation to try to ensure that the network can sufficiently learn the distribution of all view categories without overfitting to the training data. In some embodiments, after finalizing the network architecture, the network may be trained on all of the images stored in the location 640 of the storage memory 604.

In various embodiments, the shared layer 362 and the view category specific layers 370, 372, 374, 376, and 378 may be trained simultaneously. In some embodiments, batch training may be used and each batch may consist of eight sequences (or groups of images) from each view, for example, wherein each sequence is a set of 20 consecutive gray-scale images of 200×200 pixels, with no preprocessing applied to the images.

In some embodiments, the neural networks may be trained using the adam optimizer with hyper-parameters as suggested by Kingma, D. P., Ba, J. L.: Adam: a Method for Stochastic Optimization, International Conference on Learning Representations 2015 pp. 1-15 (2015). The weight of the conv layers may be initialized randomly from a zero-mean Gaussian distribution. To try to prevent the neural network from overfitting on the training data, $l_2$ norm regularization may be added to the weights of the conv kernels. In some embodiments, Keras deep learning library with TensorFlow™ backend, may be used to train and test the models.

In some embodiments, to prevent co-adaptation of features and overfitting on the training data, a dropout layer with the dropout probability of 0.5 may be used after the third pooling layer.

After training has been completed, the sets of parameters stored in the location 646 of the storage memory 104 may represent a trained echocardiographic image quality assessment neural network that includes shared layers and a plurality of view category specific layers.

Referring back to FIG. 16, in some embodiments, the flowchart 700 may include a further block 708 which directs the trainer processor 600 to produce signals representing the parameters defining the trained neural networks for causing the parameters to be provided to a system or device configured to apply the neural networks. In some embodiments, for example, block 708 may direct the trainer processor 600 to retrieve the neural network records from the location 644 and to produce signals representing the records for causing the records to be provided to the analyzer 12.

For example, in some embodiments, block 708 may direct the trainer processor 600 to retrieve the common neural network record and the view category specific neural network records stored in the location 644 and transmit signals representing the records to the analyzer 12 via the interface 624 and the network 126. Alternatively, in some embodiments, block 708 may direct the trainer processor 600 to cause the records to be stored in removable memory which may be provided to the analyzer 12.

The analyzer 12 may be configured as described above to receive the neural network records and to perform image assessment by applying the neural networks represented thereby.

In some embodiments, the block of codes 660 of the program memory 602 shown in FIG. 16 may include a block that directs the trainer processor 600 to train a view category determining neural network that is configured to take as an input at least one echocardiographic image and to output an indication of what view category should be associated with the input at least one echocardiographic image. The block may use the image data from the training image files stored in the location 640 of the storage memory 104 as inputs and indications of the associated view categories (as determined by the view category identifiers included in the image files) as desired outputs.

The neural network may include convolutional layers, max-pooling layers, and fully connected layers, the fully connected layers including a softmax layer as an output layer having outputs which represent respective determinations that an input set of echocardiographic images fall within a particular view category. In some embodiments, the block may direct the trainer processor 600 to store parameters defining the trained neural network in a view category determining neural network record in the location 648 of the storage memory 604.

Embodiments Using Distributed Processing and/or Separate Devices

In some embodiments, separation of the neural network trainer 502, the training image source 504, and the analyzer 12 into different computers or systems may facilitate control of and access to information. This may be particularly desirable with the systems described herein where personal and/or confidential information may be managed. Further, in some embodiments, separation of the neural network training from the analysis, for example, may allow different or faster computers to train the neural network.

Figure 19:
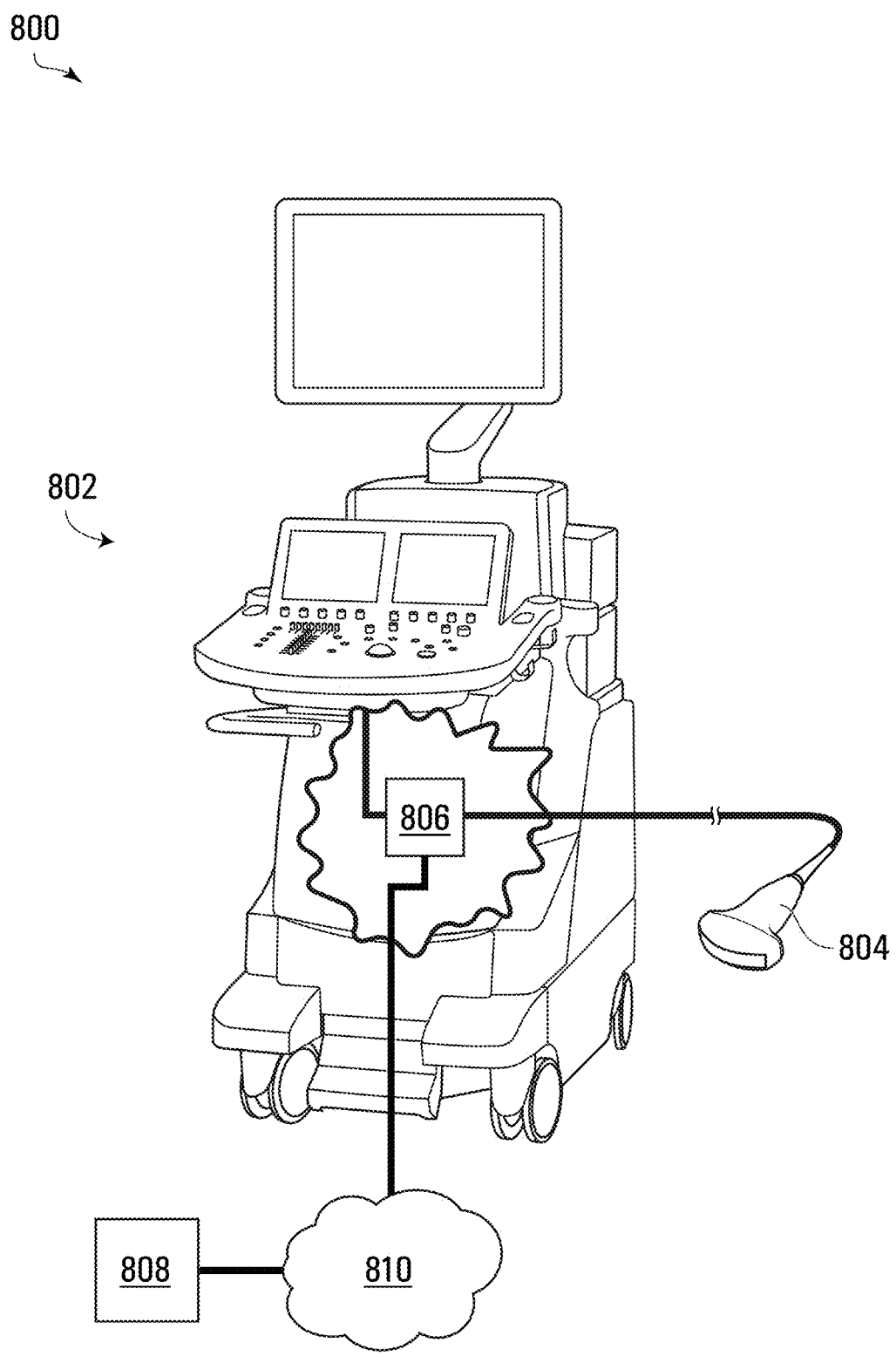
FIG. 19 is a schematic view of a system for facilitating echocardiographic image analysis in accordance with various embodiments of the invention.

In some embodiments, the functionality of aspects of the system 10 and/or the system 500 may be further modularized and/or distributed between different devices. For example, in some embodiments, a system 800 as shown in FIG. 19 may perform generally similar functions to the system 10 shown in FIG. 1. The system 800 includes a user interface system 802 generally similar to the user interface system 14 shown in FIG. 1, and a transducer 804 generally similar to the transducer 16 shown in FIG. 1. The system 800 also includes a scanner 806 and an image analyzer 808 which are in communication with one another via a network 810 and configured to together perform generally similar functions to the analyzer 12 described above. The scanner 806 may be configured to receive signals from the transducer and generate and store echocardiographic images in memory generally as described above. The scanner 806 may be configured to send the echocardiographic images to the image analyzer 808 which is configured to receive the images from the scanner 806 and generally perform image analysis steps as described above with reference to the flowchart 200 shown in FIG. 3. The image analyzer 808 may be configured to send signals to the scanner 806 for causing the scanner 806 to cause representations of the echocardiographic images and associated quality assessment values to be displayed on the display of the user interface system 802.

In some embodiments, the functionality of any or all of the devices included in the systems 10, 500, and/or 800 as shown in FIGS. 1, 13, and 18 may be performed by multiple devices which are in communication with one another via a network. In such embodiments, the devices may be distributed in a cloud computing context, for example. For example, in some embodiments, a system that functions generally similar to the system 800 shown in FIG. 19 may include a mobile device, such as a smart phone, acting similar to the user interface system 802, in communication with a scanner generally similar to the scanner 806, via a wireless connection, for example. An image analyzer acting as the image analyzer 808 may be remotely located in comparison to the scanner and the mobile device and may be in communication with the scanner 806 and/or the mobile device via a network connection, for example, over the Internet. In some embodiments, allowing the image analyzer 808 to be remotely located and accessible via a network, may facilitate the use of low cost or fast computing resources to carry the load of intensive processing during training and/or application of the neural networks.

In some embodiments, execution of block 206 may be performed by more than one analyzer device. For example, in some embodiments a first analyzer may apply the shared layers of an image quality assessment neural network to the received at least one echocardiographic image and then send the output of the shared layers to a second analyzer, which may apply one of the view specific layers to the received output. In such embodiments, the shared layers may act as a small neural network. In some embodiments, the shared layers may facilitate data compression. In some embodiments, the first analyzer may be in communication with the second analyzer via a network connection, such as, for example, an Internet connection. In some embodiments, the first analyzer may be implemented on a mobile device and the second analyzer may be in the cloud. In various embodiments, using a neural network with common shared layers may facilitate compressing the echocardiographic image data before sending the data to the second analyzer and may reduce the bandwidth needed to transfer data to the second analyzer.

In some embodiments, the first analyzer may use the shared layers of a neural network to generate a coarse quality score, and a finer quality score may be calculated by a larger architecture which is deployed in the cloud, for example, and uses the output of the shared layers.

Stored Image Analysis

In some embodiments, the analyzer 12 may be used to analyze stored images, rather than echocardiographic images received in real-time or near real-time. For example, in some embodiments, the analyzer 12 may be in communication with an image source, which may, for example, be implemented as a PACS. In some embodiments, the analyzer 12 may be in communication with the image source via a network, such as, the Internet, for example. In some embodiments, the analyzer 12 may be integrated with the image source as a single device.

In some embodiments where the analyzer 12 is used to analyze stored images from an image source, block 202 may direct the analyzer processor 100 to receive at least one echocardiographic image from the image source. Blocks 204 and 206 may direct the analyzer processor 100 to perform functions generally as described above. In some embodiments, block 208 may direct the analyzer processor 100 to produce signals for causing the quality assessment value to be stored in association with the at least one echocardiographic image at the image source. In some embodiments, using the analyzer 12 to analyze stored echocardiographic images from an image source may facilitate use of the previously captured echocardiographic images for later quantified clinical measurement of anatomical features and/or to assist in diagnosing a medical condition or a characteristic of the heart.

Embodiments Using Integrated Devices

In some embodiments, the functionality of some or all of the neural network trainer 502, the training image source 504 and/or the analyzer 12 of the systems 500 and 10 may be provided by a single integrated device or system, for example. By way of example, in various embodiments, aspects of the neural network trainer 502 and the analyzer 12 may be integrated, such that a single device performs the neural network training and the analysis. In some embodiments, some of the blocks of code may be altered and/or omitted to facilitate the execution of the functionality of the processes described herein by one or more integrated device or system. In some embodiments, a system including such integrated devices may provide advantages such as, for example, reduction in implementation and/or operating costs.

3D Representations

In some embodiments, block 202 may direct the analyzer processor 100 to receive or derive one or more 3D model representations of the patient's heart from the signals received from the scanner 16. In such embodiments, each of the 3D model representations may represent one or more echocardiographic images which may be derived or extracted from the 3D model representation by taking slices or planar sections from the 3D model, for example. In such embodiments, the flowchart 200 may be executed to analyze echocardiographic images derived or extracted from the 3D model representation.

Various Embodiments

In some embodiments, echocardiographers may have previously provided the expert quality assessment values, and the training image source 504 may store respective expert quality assessment values in association with each of the images. In such embodiments, block 704 may direct the trainer processor 600 to receive the expert quality assessment values from the training image source 504.

Certain embodiments of the systems 10, 500, and 800 have been described above, wherein a plurality of images, in some embodiments a sequence of 20 images, for example, are analyzed together to generate a single quality assessment value. In various embodiments, analyzing more than one image together may facilitate determining accurate and contextualized quality assessment values.

However, in some embodiments, the systems 10, 500, or 800 may be configured to analyze a single image at a time. In such embodiments, the flowchart 200 shown in FIG. 3, or a generally similar flowchart, may be executed to determine a quality assessment value for a single image received at block 202 of the flowchart 200. In various embodiments, analyzing a single image at a time may facilitate fast processing of the flowchart 200 and/or real-time or near real-time feedback for the operator. In embodiments where a single image is analyzed at a time, the systems 10, 500, and/or 800 may be configured to train and/or apply functions or neural networks to the single image to determine quality assessment values of each image. In such embodiments, different neural networks from those shown in FIGS. 6 and 8, as defined by different neural network records, may be trained and applied.

Figure 20:
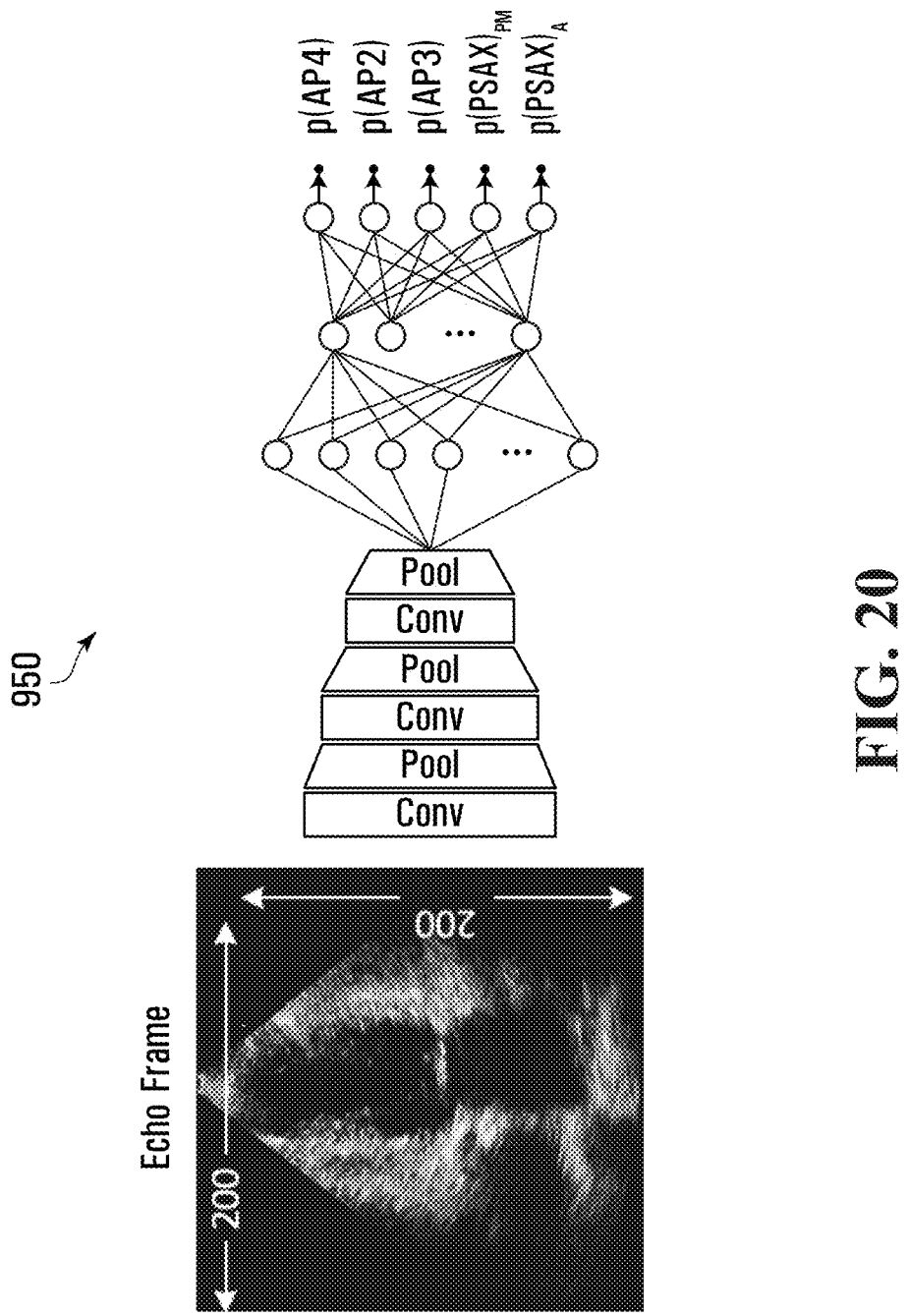
FIG. 20 is a representation of an exemplary view category determining neural network that may be used in the system shown in FIG. 1.

For example, an exemplary view category determining neural network that may be trained and/or applied to a single echocardiographic image to determine a view category to be associated with the echocardiographic image, in accordance with some embodiments, is shown at 950 in FIG. 20. In some embodiments, the neural network 950 may be configured to take as input an image having a size of 200×200 pixels, and may include one convolutional layer with 12 kernels of each 11×11 pixels, one pooling layer with a kernel of 3×3 and stride of 2, one convolutional layer with 24 kernels of each 7×7 pixels, one pooling layer with a kernel of 3×3 and stride of 2, one convolutional layer with 48 kernels of each 3×3 pixels, one pooling layer with a kernel of 3×3 and stride of 2, a fully connected layer with 2048 outputs, a fully connected layer with 1024 outputs, and a fully connected layer with 5 outputs.

Figure 21:
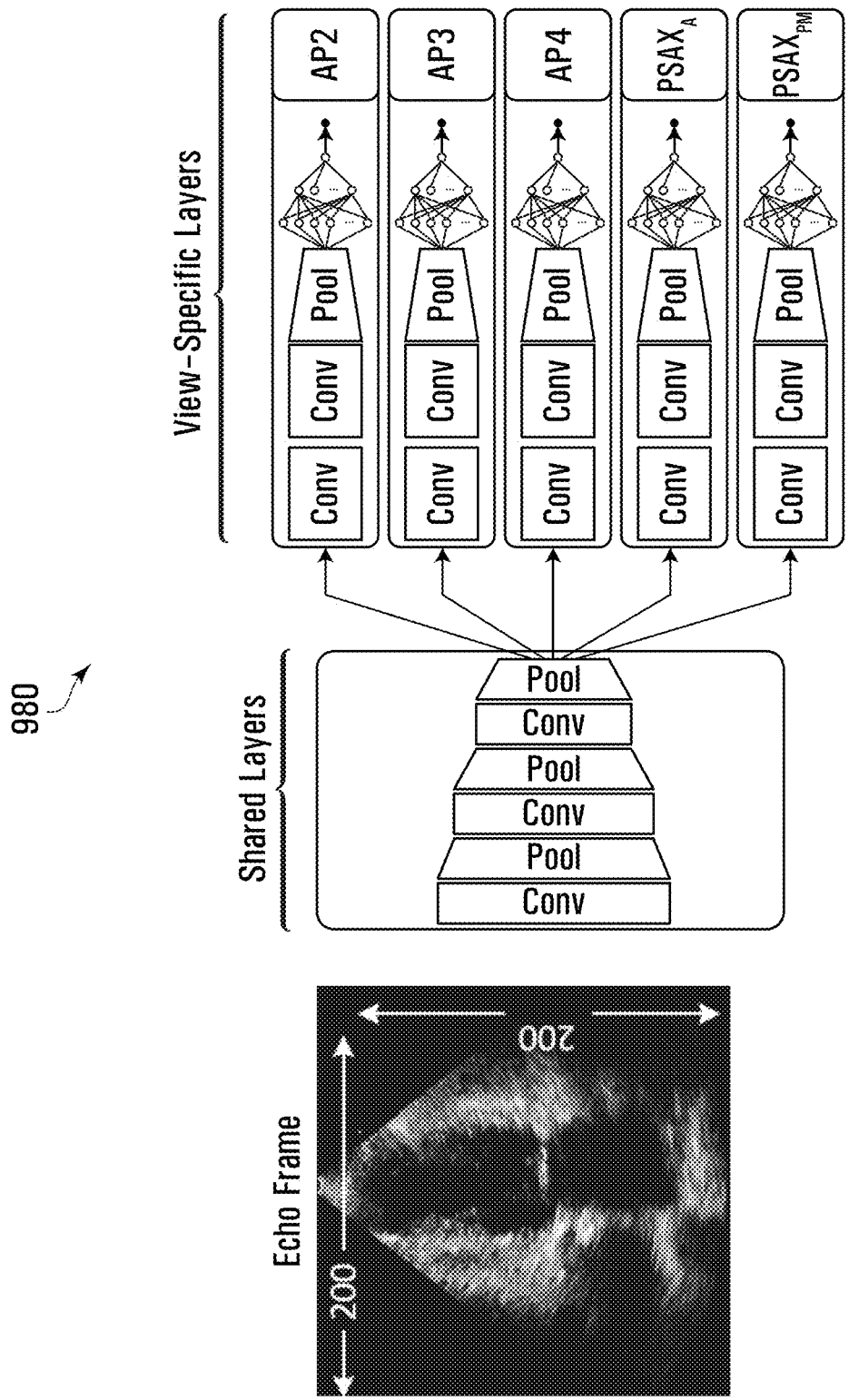
FIG. 21 is a representation of an exemplary image quality assessment neural network that may be used in the system shown in FIG. 1.

An exemplary image assessment neural network that may be trained and/or applied to a single echocardiographic image to determine a quality assessment value for the echocardiographic image, in accordance with some embodiments, is shown at 980 in FIG. 21.

While specific embodiments of the invention have been described and illustrated, such embodiments should be considered illustrative of the invention only and not as limiting the invention as construed in accordance with the accompanying claims.

The series of paragraphs below recites various illustrative combinations of features of the present disclosure. These paragraphs are intended to represent a non-limiting presentation of suitable combinations, and are alphanumerically designated for clarity and efficiency:

A0. A computer-implemented system for facilitating echocardiographic image analysis, the system comprising at least one processor configured to:
  receive signals representing a first at least one echocardiographic image;
  associate the first at least one echocardiographic image with a first view category of a plurality of predetermined echocardiographic image view categories;
  determine, based on the first at least one echocardiographic image and the first view category, a first quality assessment value representing a view category specific quality assessment of the first at least one echocardiographic image;
  produce signals representing the first quality assessment value for causing the first quality assessment value to be associated with the first at least one echocardiographic image;
  receive signals representing a second at least one echocardiographic image;
  associate the second at least one echocardiographic image with a second view category of the plurality of predetermined echocardiographic image view categories, said second view category being different from the first view category;
  determine, based on the second at least one echocardiographic image and the second view category, a second quality assessment value representing a view category specific quality assessment of the second at least one echocardiographic image; and
  produce signals representing the second quality assessment value for causing the second quality assessment value to be associated with the second at least one echocardiographic image.

A1. The system of paragraph A0 wherein the first quality assessment value represents an assessment of suitability of the first at least one echocardiographic image for quantified clinical measurement of anatomical features and wherein the second quality assessment value represents an assessment of suitability of the second at least one echocardiographic image for quantified measurement of anatomical features.

A2. The system of paragraph A0 or A1 wherein the at least one processor is configured to:
  produce signals for causing a representation of the first quality assessment value to be transmitted to at least one display for causing the at least one display to display the first quality assessment value in association with the first at least one echocardiographic image, to assist one or more operators of an echocardiographic device in capturing at least one subsequent echocardiographic image; and
  produce signals for causing a representation of the second quality assessment value to be transmitted to the at least one display for causing the at least one display to display the second quality assessment value in association with the second at least one echocardiographic image, to assist the one or more operators in capturing at least one subsequent echocardiographic image.

A3. The system of any one of paragraphs A0 to A2 wherein the at least one processor is configured to:
apply one or more view categorization functions to the first at least one echocardiographic image to determine that the first at least one echocardiographic image falls within the first view category; and
apply one or more view categorization functions to the second at least one echocardiographic image to determine that the second at least one echocardiographic image falls within the second view category.

A4. The system of any one of paragraphs A0 to A3 wherein the first at least one echocardiographic image comprises a plurality of echocardiographic images and wherein the at least one processor is configured to determine the first quality assessment value by determining a single quality assessment value representing a view category specific assessment of the plurality of echocardiographic images.

A5. The system of any one of paragraphs A0 to A4 wherein each of the plurality of predetermined echocardiographic image view categories is associated with a respective set of assessment parameters and wherein the at least one processor is configured to:
determine that a first set of assessment parameters of the sets of assessment parameters is associated with the first view category;
in response to determining that the first set of assessment parameters is associated with the first view category, apply a first function based on the first set of assessment parameters to the first at least one echocardiographic image;
determine that a second set of assessment parameters of the sets of assessment parameters is associated with the second view category; and
in response to determining that the second set of assessment parameters is associated with the second view category, apply a second function based on the second set of assessment parameters to the second at least one echocardiographic image.

A6. The system of paragraph A5 wherein each of the sets of assessment parameters includes:
a set of common assessment parameters, which are common to each of the sets of assessment parameters; and
a set of view category specific assessment parameters, which are unique to the set of assessment parameters.

A7. The system of paragraph A5 or A6 wherein each of the sets of assessment parameters is a set of neural network parameters that defines a neural network having a plurality of layers including an input layer configured to receive one or more echocardiographic images and an output layer configured to output one or more quality assessment values and wherein the at least one processor is configured to:
apply the first function based on the first set of assessment parameters to the first at least one echocardiographic image by inputting the first at least one echocardiographic image into the neural network defined by the first set of assessment parameters; and
apply the second function based on the second set of assessment parameters to the second at least one echocardiographic image by inputting the second at least one echocardiographic image into the neural network defined by the second set of assessment parameters.

A8. The system of paragraph A7 wherein the at least one processor is configured to train the neural networks by:
receiving signals representing a plurality of echocardiographic training images, each of the plurality of echocardiographic training images associated with one of the plurality of predetermined echocardiographic image view categories;
receiving signals representing respective expert quality assessment values representing view category specific quality assessments of the plurality of echocardiographic training images, each of the expert quality assessment values provided by an expert echocardiographer and associated with one of the plurality of echocardiographic training images; and
training the neural networks using the plurality of echocardiographic training images as inputs and the associated expert quality assessment values as desired outputs to determine the sets of neural network parameters defining the neural networks.

A9. The system of paragraph A8 wherein each of the expert quality assessment values represents an assessment of suitability of the associated echocardiographic image for quantified clinical measurement of anatomical features.

A10. The system of paragraph A8 or A9 wherein the at least one processor is configured to derive each of the expert quality assessment values at least in part from a clinical plane assessment value representing an expert opinion whether the associated echocardiographic training image was taken in an anatomical plane suitable for quantified clinical measurement of anatomical features.

A11. The system of any one of paragraphs A8 to A10 wherein each of the sets of neural network parameters includes:
a set of common neural network parameters, which are common to each of the sets of neural network parameters; and
a set of view category specific neural network parameters, which are unique to the set of neural network parameters; and
wherein the at least one processor is configured to, for each echocardiographic training image:
select one of the sets of view category specific neural network parameters based on the predetermined echocardiographic image view category associated with the echocardiographic training image; and
using the echocardiographic training image as an input and the associated expert quality assessment values as a desired output, train a neural network defined by the set of common neural network parameters and the selected one of the sets of view category specific neural network parameters to update the set of common neural network parameters and the selected one of the sets of view category specific neural network parameters.

B0. A computer-implemented system for training neural networks to facilitate echocardiographic image analysis, the system comprising at least one processor configured to:
receive signals representing a plurality of echocardiographic training images, each of the plurality of echocardiographic training images associated with one of a plurality of predetermined echocardiographic image view categories;
receive signals representing expert quality assessment values representing view category specific quality assessments of the plurality of echocardiographic training images, each of the expert quality assessment values provided by an expert echocardiographer and associated with one of the plurality of echocardiographic training images; and train the neural networks using the plurality of echocardiographic training images and the associated expert quality assessment values to determine sets of neural network parameters defining the neural networks, at least a portion of each of said neural networks associated with one of the plurality of predetermined echocardiographic image view categories.

B1. The system of paragraph B0 wherein each of the expert quality assessment values represents an assessment of suitability of the associated echocardiographic image for quantified clinical measurement of anatomical features.

B2. The system of paragraph B0 or B1 wherein the at least one processor is configured to derive each of the expert quality assessment values at least in part from a clinical plane assessment value representing an expert opinion whether the associated echocardiographic training image was taken in an anatomical plane suitable for a quantified clinical measurement of anatomical features.

B3. The system of any one of paragraphs B0 to B2 wherein each of the sets of neural network parameters includes:
  a set of common neural network parameters, which are common to each of the sets of neural network parameters; and
  a set of view category specific neural network parameters, which are unique to the set of neural network parameters; and
wherein the at least one processor is configured to, for each echocardiographic training image:
  select one of the sets of view category specific neural network parameters based on the predetermined echocardiographic image view category associated with the echocardiographic training image; and
  using the echocardiographic training image as an input and the associated expert quality assessment value as a desired output, train a neural network defined by the set of common neural network parameters and the selected one of the sets of view category specific neural network parameters to update the set of common neural network parameters and the selected one of the sets of view category specific neural network parameters.

C0. A computer-implemented method of facilitating echocardiographic image analysis, the method comprising:
  receiving signals representing a first at least one echocardiographic image;
  associating the first at least one echocardiographic image with a first view category of a plurality of predetermined echocardiographic image view categories;
  determining, based on the first at least one echocardiographic image and the first view category, a first quality assessment value representing a view category specific quality assessment of the first at least one echocardiographic image;
  producing signals representing the first quality assessment value for causing the first quality assessment value to be associated with the first at least one echocardiographic image;
  receiving signals representing a second at least one echocardiographic image;
  associating the second at least one echocardiographic image with a second view category of the plurality of predetermined echocardiographic image view categories, said second view category being different from the first view category;
  determining, based on the second at least one echocardiographic image and the second view category, a second quality assessment value representing a view category specific quality assessment of the second at least one echocardiographic image; and
  producing signals representing the second quality assessment value for causing the second quality assessment value to be associated with the second at least one echocardiographic image.

C1. The method of paragraph C0 wherein the first quality assessment value represents an assessment of suitability of the first at least one echocardiographic image for quantified clinical measurement of anatomical features and wherein the second quality assessment value represents an assessment of suitability of the second at least one echocardiographic image for quantified measurement of anatomical features.

C2. The method of paragraph C0 or C1 wherein:
  producing the signals representing the first quality assessment value comprises producing signals for causing a representation of the first quality assessment value to be transmitted to at least one display for causing the at least one display to display the first quality assessment value in association with the first at least one echocardiographic image, to assist one or more operators of an echocardiographic device in capturing at least one subsequent echocardiographic image; and
  producing the signals representing the second quality assessment value comprises producing signals for causing a representation of the second quality assessment value to be transmitted to the at least one display for causing the at least one display to display the second quality assessment value in association with the second at least one echocardiographic image, to assist the one or more operators in capturing at least one subsequent echocardiographic image.

C3. The method of any one of paragraphs C0 to C2 wherein:
  associating the first at least one echocardiographic image with the first view category comprises applying one or more view categorization functions to the first at least one echocardiographic image to determine that the first at least one echocardiographic image falls within the first view category; and
  associating the second at least one echocardiographic image with the second view category comprises applying one or more view categorization functions to the second at least one echocardiographic image to determine that the second at least one echocardiographic image falls within the second view category.

C4. The method of any one of paragraphs C0 to C3 wherein the first at least one echocardiographic image comprises a plurality of echocardiographic images and wherein determining the first quality assessment value comprises determining a single quality assessment value representing a view category specific assessment of the plurality of echocardiographic images.

C5. The method of any one of paragraphs C0 to C4 wherein each of the plurality of predetermined echocardiographic image view categories is associated with a respective set of assessment parameters and wherein:
  determining the first quality assessment value comprises:
    determining that a first set of assessment parameters of the sets of assessment parameters is associated with the first view category; and
    in response to determining that the first set of assessment parameters is associated with the first view category, applying a first function based on the first set of assessment parameters to the first at least one echocardiographic image; and determining the second quality assessment value comprises:
  determining that a second set of assessment parameters of the sets of assessment parameters is associated with the second view category; and
  in response to determining that the second set of assessment parameters is associated with the second view category, applying a second function based on the second set of assessment parameters to the second at least one echocardiographic image.

C6. The method of paragraph C5 wherein each of the sets of assessment parameters includes:
  a set of common assessment parameters, which are common to each of the sets of assessment parameters; and
  a set of view category specific assessment parameters, which are unique to the set of assessment parameters.

C7. The method of paragraph C5 or C6 wherein each of the sets of assessment parameters is a set of neural network parameters that defines a neural network having a plurality of layers including an input layer configured to receive one or more echocardiographic images and an output layer configured to output one or more quality assessment values and wherein:
  applying the first function based on the first set of assessment parameters to the first at least one echocardiographic image comprises inputting the first at least one echocardiographic image into the neural network defined by the first set of assessment parameters; and applying the second function based on the second set of assessment parameters to the second at least one echocardiographic image comprises inputting the second at least one echocardiographic image into the neural network defined by the second set of assessment parameters.

C8. The method of paragraph C7 further comprising training the neural networks, said training comprising:
  receiving signals representing a plurality of echocardiographic training images, each of the plurality of echocardiographic training images associated with one of the plurality of predetermined echocardiographic image view categories;
  receiving signals representing respective expert quality assessment values representing view category specific quality assessments of the plurality of echocardiographic training images, each of the expert quality assessment values provided by an expert echocardiographer and associated with one of the plurality of echocardiographic training images; and
  training the neural networks using the plurality of echocardiographic training images as inputs and the associated expert quality assessment values as desired outputs to determine the sets of neural network parameters defining the neural networks.

C9. The method of paragraph C8 wherein each of the expert quality assessment values represents an assessment of suitability of the associated echocardiographic image for quantified clinical measurement of anatomical features.

C10. The method of paragraph C8 or C9 further comprising deriving each of the expert quality assessment values at least in part from a clinical plane assessment value representing an expert opinion whether the associated echocardiographic training image was taken in an anatomical plane suitable for quantified clinical measurement of anatomical features.

C11. The method of any one of paragraphs C8 to C10 wherein each of the sets of neural network parameters includes:
  a set of common neural network parameters, which are common to each of the sets of neural network parameters; and
  a set of view category specific neural network parameters, which are unique to the set of neural network parameters; and
  wherein training the neural networks using the plurality of echocardiographic training images and the associated expert quality assessment values comprises, for each echocardiographic training image:
  selecting one of the sets of view category specific neural network parameters based on the predetermined echocardiographic image view category associated with the echocardiographic training image; and
  using the echocardiographic training image as an input and the associated expert quality assessment values as a desired output, training a neural network defined by the set of common neural network parameters and the selected one of the sets of view category specific neural network parameters to update the set of common neural network parameters and the selected one of the sets of view category specific neural network parameters.

D0. A computer-implemented method of training neural networks to facilitate echocardiographic image analysis, the method comprising:
  receiving signals representing a plurality of echocardiographic training images, each of the plurality of echocardiographic training images associated with one of a plurality of predetermined echocardiographic image view categories;
  receiving signals representing expert quality assessment values representing view category specific quality assessments of the plurality of echocardiographic training images, each of the expert quality assessment values provided by an expert echocardiographer and associated with one of the plurality of echocardiographic training images; and
  training the neural networks using the plurality of echocardiographic training images and the associated expert quality assessment values to determine sets of neural network parameters defining the neural networks, at least a portion of each of said neural networks associated with one of the plurality of predetermined echocardiographic image view categories.

D1. The method of paragraph D0 wherein each of the expert quality assessment values represents an assessment of suitability of the associated echocardiographic image for quantified clinical measurement of anatomical features.

D2. The method of paragraph D0 or D1 further comprising deriving each of the expert quality assessment values at least in part from a clinical plane assessment value representing an expert opinion whether the associated echocardiographic training image was taken in an anatomical plane suitable for a quantified clinical measurement of anatomical features.

D3. The method of any one of paragraphs D0 to D2 wherein each of the sets of neural network parameters includes:
  a set of common neural network parameters, which are common to each of the sets of neural network parameters; and
  a set of view category specific neural network parameters, which are unique to the set of neural network parameters; and wherein training the neural networks using the plurality of echocardiographic training images and the associated expert quality assessment values comprises, for each echocardiographic training image:
  selecting one of the sets of view category specific neural network parameters based on the predetermined echocardiographic image view category associated with the echocardiographic training image; and
  using the echocardiographic training image as an input and the associated expert quality assessment value as a desired output, training a neural network defined by the set of common neural network parameters and the selected one of the sets of view category specific neural network parameters to update the set of common neural network parameters and the selected one of the sets of view category specific neural network parameters.

D4. A computer readable medium having stored thereon codes which when executed by at least one processor cause the at least one processor to perform the method of any one of paragraphs C0 to D3.

E0. A system for facilitating echocardiographic image analysis, the system comprising:
  means for receiving signals representing a first at least one echocardiographic image;
  means for associating the first at least one echocardiographic image with a first view category of a plurality of predetermined echocardiographic image view categories;
  means for determining, based on the first at least one echocardiographic image and the first view category, a first quality assessment value representing a view category specific quality assessment of the first at least one echocardiographic image;
  means for producing signals representing the first quality assessment value for causing the first quality assessment value to be associated with the first at least one echocardiographic image;
  means for receiving signals representing a second at least one echocardiographic image;
  means for associating the second at least one echocardiographic image with a second view category of the plurality of predetermined echocardiographic image view categories, said second view category being different from the first view category;
  means for determining, based on the second at least one echocardiographic image and the second view category, a second quality assessment value representing a view category specific quality assessment of the second at least one echocardiographic image; and
  means for producing signals representing the second quality assessment value for causing the second quality assessment value to be associated with the second at least one echocardiographic image.

F0. A system for training neural networks to facilitate echocardiographic image analysis, the system comprising:
  means for receiving signals representing a plurality of echocardiographic training images, each of the plurality of echocardiographic training images associated with one of a plurality of predetermined echocardiographic image view categories;
  means for receiving signals representing expert quality assessment values representing view category specific quality assessments of the plurality of echocardiographic training images, each of the expert quality assessment values provided by an expert echocardiographer and associated with one of the plurality of echocardiographic training images; and
  means for training the neural networks using the plurality of echocardiographic training images and the associated expert quality assessment values to determine sets of neural network parameters defining the neural networks, at least a portion of each of said neural networks associated with one of the plurality of predetermined echocardiographic image view categories.

The invention claimed is:

1. A computer-implemented system for facilitating echocardiographic image analysis, the system comprising at least one processor configured to:
  receive signals representing a first at least one echocardiographic image;
  associate the first at least one echocardiographic image with a first view category of a plurality of predetermined echocardiographic image view categories;
  determine, based on the first at least one echocardiographic image and the first view category, a first quality assessment value representing a view category specific quality assessment of the first at least one echocardiographic image;
  produce signals representing the first quality assessment value for causing the first quality assessment value to be associated with the first at least one echocardiographic image;
  receive signals representing a second at least one echocardiographic image;
  associate the second at least one echocardiographic image with a second view category of the plurality of predetermined echocardiographic image view categories, said second view category being different from the first view category;
  determine, based on the second at least one echocardiographic image and the second view category, a second quality assessment value representing a view category specific quality assessment of the second at least one echocardiographic image; and
  produce signals representing the second quality assessment value for causing the second quality assessment value to be associated with the second at least one echocardiographic image;
  wherein each of the plurality of predetermined echocardiographic image view categories is associated with a respective set of assessment parameters, each of the sets of assessment parameters being a set of neural network parameters that define a neural network having a plurality of layers including an input layer configured to receive one or more echocardiographic images and an output layer configured to output one or more quality assessment values, and wherein the at least one processor is configured to determine the first quality assessment value by:
    determining that a first set of assessment parameters of the sets of assessment parameters is associated with the first view category; and
    in response to determining that the first set of assessment parameters is associated with the first view category, inputting the first at least one echocardiographic image into the neural network defined by the first set of assessment parameters; and
  wherein the at least one processor is configured to determine the second quality assessment value by:
    determining that a second set of assessment parameters of the sets of assessment parameters is associated with the second view category; and
    in response to determining that the second set of assessment parameters is associated with the second view category, inputting the second at least one echocardiographic image into the neural network defined by the second set of assessment parameters.

2. The system of claim 1 wherein the first quality assessment value represents an assessment of suitability of the first at least one echocardiographic image for quantified clinical measurement of anatomical features and wherein the second quality assessment value represents an assessment of suitability of the second at least one echocardiographic image for quantified measurement of anatomical features.

3. The system of claim 1 wherein the at least one processor is configured to:
produce signals for causing a representation of the first quality assessment value to be transmitted to at least one display for causing the at least one display to display the first quality assessment value in association with the first at least one echocardiographic image, to assist one or more operators of an echocardiographic device in capturing at least one subsequent echocardiographic image; and
produce signals for causing a representation of the second quality assessment value to be transmitted to the at least one display for causing the at least one display to display the second quality assessment value in association with the second at least one echocardiographic image, to assist the one or more operators in capturing at least one subsequent echocardiographic image.

4. The system of claim 1 wherein the at least one processor is configured to:
apply one or more view categorization functions to the first at least one echocardiographic image to determine that the first at least one echocardiographic image falls within the first view category; and
apply one or more view categorization functions to the second at least one echocardiographic image to determine that the second at least one echocardiographic image falls within the second view category.

5. The system of claim 1 wherein the first at least one echocardiographic image comprises a plurality of echocardiographic images and wherein the at least one processor is configured to determine the first quality assessment value by determining a single quality assessment value representing a view category specific assessment of the plurality of echocardiographic images.

6. The system of claim 1 wherein each of the sets of assessment parameters includes:
a set of common assessment parameters, which are common to each of the sets of assessment parameters; and
a set of view category specific assessment parameters, which are unique to the set of assessment parameters.

7. The system of claim 1 wherein the at least one processor is configured to train the neural networks by:
receiving signals representing a plurality of echocardiographic training images, each of the plurality of echocardiographic training images associated with one of the plurality of predetermined echocardiographic image view categories;
receiving signals representing respective expert quality assessment values representing view category specific quality assessments of the plurality of echocardiographic training images, each of the expert quality assessment values provided by an expert echocardiographer and associated with one of the plurality of echocardiographic training images; and
training the neural networks using the plurality of echocardiographic training images as inputs and the associated expert quality assessment values as desired outputs to determine the sets of neural network parameters defining the neural networks.

8. The system of claim 7 wherein each of the expert quality assessment values represents an assessment of suitability of the associated echocardiographic image for quantified clinical measurement of anatomical features.

9. The system of claim 7 wherein the at least one processor is configured to derive each of the expert quality assessment values at least in part from a clinical plane assessment value representing an expert opinion whether the associated echocardiographic training image was taken in an anatomical plane suitable for quantified clinical measurement of anatomical features.

10. The system of claim 7 wherein each of the sets of neural network parameters includes:
a set of common neural network parameters, which are common to each of the sets of neural network parameters; and
a set of view category specific neural network parameters, which are unique to the set of neural network parameters; and
wherein the at least one processor is configured to, for each echocardiographic training image:
select one of the sets of view category specific neural network parameters based on the predetermined echocardiographic image view category associated with the echocardiographic training image; and
using the echocardiographic training image as an input and the associated expert quality assessment values as a desired output, train a neural network defined by the set of common neural network parameters and the selected one of the sets of view category specific neural network parameters to update the set of common neural network parameters and the selected one of the sets of view category specific neural network parameters.

11. A computer-implemented system for training neural networks to facilitate echocardiographic image analysis, the system comprising at least one processor configured to:
receive signals representing a plurality of echocardiographic training images, each of the plurality of echocardiographic training images associated with one of a plurality of predetermined echocardiographic image view categories;
receive signals representing expert quality assessment values representing view category specific quality assessments of the plurality of echocardiographic training images, each of the expert quality assessment values provided by an expert echocardiographer and associated with one of the plurality of echocardiographic training images; and
train the neural networks using the plurality of echocardiographic training images and the associated expert quality assessment values to determine sets of neural network parameters defining the neural networks, at least a portion of each of said neural networks associated with one of the plurality of predetermined echocardiographic image view categories;
wherein the at least one processor is further configured to, once the neural networks are trained:
receive signals representing a first at least one echocardiographic image;
associate the first at least one echocardiographic image with a first view category of a plurality of predetermined echocardiographic image view categories;
determine, based on the first at least one echocardiographic image and the first view category, a first quality assessment value representing a view category specific quality assessment of the first at least one echocardiographic image;

produce signals representing the first quality assessment value for causing the first quality assessment value to be associated with the first at least one echocardiographic image;

receive signals representing a second at least one echocardiographic image;

associate the second at least one echocardiographic image with a second view category of the plurality of predetermined echocardiographic image view categories, said second view category being different from the first view category;

determine, based on the second at least one echocardiographic image and the second view category, a second quality assessment value representing a view category specific quality assessment of the second at least one echocardiographic image; and produce signals representing the second quality assessment value for causing the second quality assessment value to be associated with the second at least one echocardiographic image;

wherein each of the plurality of predetermined echocardiographic image view categories is associated with a respective set of assessment parameters, each of the sets of assessment parameters being a set of neural network parameters that define a neural network having a plurality of layers including an input layer configured to receive one or more echocardiographic images and an output layer configured to output one or more quality assessment values, and wherein the at least one processor is configured to determine the first quality assessment value by:

determining that a first set of assessment parameters of the sets of assessment parameters is associated with the first view category; and in response to determining that the first set of assessment parameters is associated with the first view category, inputting the first at least one echocardiographic image into the neural network defined by the first set of assessment parameters; and wherein the at least one processor is configured to determine the second quality assessment value by:

determining that a second set of assessment parameters of the sets of assessment parameters is associated with the second view category; and in response to determining that the second set of assessment parameters is associated with the second view category, inputting the second at least one echocardiographic image into the neural network defined by the second set of assessment parameters.

12. The system of claim 11 wherein each of the expert quality assessment values represents an assessment of suitability of the associated echocardiographic image for quantified clinical measurement of anatomical features.

13. The system of claim 11 wherein the at least one processor is configured to derive each of the expert quality assessment values at least in part from a clinical plane assessment value representing an expert opinion whether the associated echocardiographic training image was taken in an anatomical plane suitable for a quantified clinical measurement of anatomical features.

14. The system of claim 11 wherein each of the sets of neural network parameters includes:

a set of common neural network parameters, which are common to each of the sets of neural network parameters; and a set of view category specific neural network parameters, which are unique to the set of neural network parameters; and wherein the at least one processor is configured to, for each echocardiographic training image:

select one of the sets of view category specific neural network parameters based on the predetermined echocardiographic image view category associated with the echocardiographic training image; and using the echocardiographic training image as an input and the associated expert quality assessment value as a desired output, train a neural network defined by the set of common neural network parameters and the selected one of the sets of view category specific neural network parameters to update the set of common neural network parameters and the selected one of the sets of view category specific neural network parameters.

15. A computer-implemented method of facilitating echocardiographic image analysis, the method comprising:

receiving signals representing a first at least one echocardiographic image;

associating the first at least one echocardiographic image with a first view category of a plurality of predetermined echocardiographic image view categories;

determining, based on the first at least one echocardiographic image and the first view category, a first quality assessment value representing a view category specific quality assessment of the first at least one echocardiographic image;

producing signals representing the first quality assessment value for causing the first quality assessment value to be associated with the first at least one echocardiographic image;

receiving signals representing a second at least one echocardiographic image;

associating the second at least one echocardiographic image with a second view category of the plurality of predetermined echocardiographic image view categories, said second view category being different from the first view category;

determining, based on the second at least one echocardiographic image and the second view category, a second quality assessment value representing a view category specific quality assessment of the second at least one echocardiographic image; and producing signals representing the second quality assessment value for causing the second quality assessment value to be associated with the second at least one echocardiographic image;

wherein each of the plurality of predetermined echocardiographic image view categories is associated with a respective set of assessment parameters, each of the sets of assessment parameters being a set of neural network parameters that defines a neural network having a plurality of layers including an input layer configured to receive one or more echocardiographic images and an output layer configured to output one or more quality assessment values and wherein:

determining the first quality assessment value comprises:

determining that a first set of assessment parameters of the sets of assessment parameters is associated with the first view category; and in response to determining that the first set of assessment parameters is associated with the first view category, inputting the first at least one echocardiographic image into the neural network defined by the first set of assessment parameters applying a first function based on the first set of assessment parameters to the first at least one echocardiographic image; and determining the second quality assessment value comprises:

determining that a second set of assessment parameters of the sets of assessment parameters is associated with the second view category; and in response to determining that the second set of assessment parameters is associated with the second view category, inputting the second at least one echocardiographic image into the neural network defined by the second set of assessment parameters.

16. The method of claim 15 wherein the first quality assessment value represents an assessment of suitability of the first at least one echocardiographic image for quantified clinical measurement of anatomical features and wherein the second quality assessment value represents an assessment of suitability of the second at least one echocardiographic image for quantified measurement of anatomical features.

17. The method of claim 15 wherein:

producing the signals representing the first quality assessment value comprises producing signals for causing a representation of the first quality assessment value to be transmitted to at least one display for causing the at least one display to display the first quality assessment value in association with the first at least one echocardiographic image, to assist one or more operators of an echocardiographic device in capturing at least one subsequent echocardiographic image; and producing the signals representing the second quality assessment value comprises producing signals for causing a representation of the second quality assessment value to be transmitted to the at least one display for causing the at least one display to display the second quality assessment value in association with the second at least one echocardiographic image, to assist the one or more operators in capturing at least one subsequent echocardiographic image.

18. The method of claim 15 wherein:

associating the first at least one echocardiographic image with the first view category comprises applying one or more view categorization functions to the first at least one echocardiographic image to determine that the first at least one echocardiographic image falls within the first view category; and associating the second at least one echocardiographic image with the second view category comprises applying one or more view categorization functions to the second at least one echocardiographic image to determine that the second at least one echocardiographic image falls within the second view category.

19. The method of claim 15 wherein the first at least one echocardiographic image comprises a plurality of echocardiographic images and wherein determining the first quality assessment value comprises determining a single quality assessment value representing a view category specific assessment of the plurality of echocardiographic images.

20. The method of claim 15 wherein each of the sets of assessment parameters includes:

a set of common assessment parameters, which are common to each of the sets of assessment parameters; and a set of view category specific assessment parameters, which are unique to the set of assessment parameters.

* * * * *